US005792610A

United States Patent [19]
Witney et al.

[11] Patent Number: 5,792,610
[45] Date of Patent: Aug. 11, 1998

[54] METHOD FOR CONDUCTING MULTIPARAMETRIC FLUORESCENCE IN SITU HYBRIDIZATION

[75] Inventors: Franklin R. Witney, Novato; David M. Heffelfinger, San Pablo, both of Calif.

[73] Assignee: BioRad Laboratories, Inc., Hercules, Calif.

[21] Appl. No.: 640,658

[22] Filed: May 1, 1996

[51] Int. Cl.[6] .............................. C12Q 1/68; G01B 9/02; G01B 11/00; G01T 3/45
[52] U.S. Cl. ........................ 435/6; 356/345; 356/346; 356/359; 356/363
[58] Field of Search ........................ 435/6; 356/317, 356/318, 345, 346, 359, 363

[56] References Cited

U.S. PATENT DOCUMENTS

| | | | |
|---|---|---|---|
| 3,924,952 | 12/1975 | Marèchal et al. | 356/106 |
| 4,410,275 | 10/1983 | Shaw et al. | 356/350 |
| 4,529,312 | 7/1985 | Pavlath et al. | 356/350 |
| 4,637,722 | 1/1987 | Kim | 356/350 |
| 4,671,658 | 6/1987 | Shaw et al. | 356/350 |
| 4,687,330 | 8/1987 | Lefevre | 356/350 |
| 4,687,732 | 8/1987 | Ward et al. | 435/6 |
| 4,711,955 | 12/1987 | Ward et al. | 536/29 |
| 4,836,676 | 6/1989 | Kim et al. | 356/350 |
| 5,108,183 | 4/1992 | Fling et al. | 356/350 |
| 5,328,824 | 7/1994 | Ward et al. | 435/6 |
| 5,449,767 | 9/1995 | Ward et al. | 536/24.3 |
| 5,539,517 | 7/1996 | Cabib et al. | 356/346 |

FOREIGN PATENT DOCUMENTS

WO90/05789  5/1990  WIPO ..................... C12Q 1/68

OTHER PUBLICATIONS

Lewis, R. (1996). FISH technology ready to leap from lab to the clinic. *Gen. Eng. News.* 16(10):1,26.

Marx, J. (1996). New methods for expanding the chromosomal paint kit. *Science.* 273:430.

Travis, J. (1996). Bringing bold color to chromosomes. *Science News.* 149:215.

Lewis, R. (1996). Chromosome charting takes a giant step. *Photonics Spectra.* 30:48.

Schröck, E. (1996). Multicolor spectral karyotyping of human chromosomes. *Science.* 273:494–497.

Speicher, M.R. (1996). Karyotyping human chromosomes by combinatorial multi–fluor FISH. *Nature Genet.* 12:368–375.

Cremer, T. et al., "Detection of chromosome aberrations in the human interphase nucleus by visualization of specific target DNAs with radioactive and non–radioactive in situ hybridization techniques: diagnosis of trisomony 18 with probe L1.84." *Hum. Genet.* 74:346–352 (1986).

Cremer, T. et al., "Role of chromosome territories in the functional compartmentalization of the cell nucleus." In: Cold Spring Harbor Symposia on Quantitative Biology, vol. LVIII, pp. 777–792, Cold Spring Harbor Laboratory Press, NY (1994).

Dauwerse, J.G. et al., "Multiple colors by fluorescence in situ hybridization using ratio–labeled DNA probes create a molecular karyotype." *Hum. Mol. Genet.* 1:539–598 (1992).

du Manoir, S. et al., "Hardware and software requirements for quantitative analysis of comparative genomic hybridization." *Cytometry* 9:4–9 (1995).

(List continued on next page.)

Primary Examiner—W. Gary Jones
Assistant Examiner—Amy Atzel
Attorney, Agent, or Firm—Jeffrey I. Auerbach; Howrey & Simon

[57] ABSTRACT

The invention relates to a method of identifying the individual autosomal and sex chromosomes of a human karyotype through the use of a set of combinatorially labeled oligonucleotide probes each member thereof: (i) having a predetermined label distinguishable from the label of any other member of said set, and (ii) being capable of specifically hybridizing with one predetermined autosomal or sex chromosome of a human karyotype.

9 Claims, 5 Drawing Sheets
(2 of 5 Drawings Filed in Color)

OTHER PUBLICATIONS du Manoir, S. et al., "Detection of complete and partial chromosome gains and losses by comparative genomic in situ hybridization." *Hum. Gent.* 90:590–610 (1993).

Ernst, L.A. et al., "Cyanine dye labeling reagents for sulfhydryl groups." *Cytometry* 10:3–10 (1989).

Guan, X.Y. et al., "Coverage of chromosome 6 by chromosome microdisection: generation of 14 subregion–specific probes." *Hum. Genetics* 95:637–640 (1995).

Ledbetter, D.H., "Localisation of pseudohypoaldosteronism genes to chromosome 16p12.2–13.1 and 12p13.1–pter by homozygosity mapping." *Hum. Mol. Genet.* 5:293–299 (1992).

Lengauer, C. et al., "Chromosome bar codes produced by multicolor fluoresence in situ hybridization with multiple YAC clones and whole chromosome painting probes." *Hum. Mol. Genet.* 2:505–512 (1993).

Manuelidis, L. et al., "Reproducible compartmentalization of individual chromosome domains in human CNS cells revealed by in situ hybridization and three–dimensional reconstruction." *Chromosoma* 96:397–410 (1988).

Mujumdar, R.B. et al., "Cyanine dye labeling reagents containing isothiocyanate group." *Cytometry* 10:11–19 (1989).

Nederlof, P.M. et al., "Multiple fluorescence in situ hybridization." *Cytometry* 11:126–131 (1990).

Nederlof, P.M. et al., "Three color fluorescence in situ hybridization for the simultaneous detection of multiple nucleic acid sequences." *Cytometry* 10:20–27 (1989).

Pinkel, D. et al., "Cytogenic analysis using quantitative, high sensitivity, fluorescence hybridization." *Proc. Natl. Acad. Sci. (U.S.A.)* 83:2934–2938 (1986).

Ried, T. et al., "Simultaneous visualization of seven different DNA probes by in situ hybridization using combinatorial fluorescence and digital imaging microscopy." *Proc. Natl. Acad. Sci. (U.S.A.)* 89:1388–1392 (1992).

Smith, T.G. et al., "Edge detection in images using Marr–Hildreth filtering techniques." *J. Neurosci. Methods* 2675–82 (1988).

Telenius, H. et al., "Cytogenic analysis by chromosome painting using DOP–PCR amplified flow–sorted chromosomes." *Genes, Chromosomes & Cancer* 4:257–263 (1992).

Waggoner, A., "Covalent labeling of proteins and nucleic acids with fluorophores." *Methods in Enzymology* 246:362–373 (1995).

Waggoner, A. et al., "Multiple spectral parameter imaging." *Methods Cell Biol.* 30:449–478 (1989).

Wiegant, J. et al., "Multiple and sensitive fluorescence in situ hybridization with rhodamine–, fluorescein–, and coumarin–labeled DNAs." *Cytogenet. Cell Genet.* 63:73–76 (1993).

Wiegant, J. et al., "In situ hybridization with fluoreceinated DNA." *Nuc. Acids Res.* 19:3237–3241 (1991).

Popp et al. (1993) Human Genetics 92:527–32.

Malik et al. (1996) Photochemistry and Photobiology 63:608–614.

METHOD FOR CONDUCTING MULTIPARAMETRIC FLUORESCENCE IN SITU HYBRIDIZATION

FIELD OF THE INVENTION

The present invention relates to nucleic acid chemistry, and more specifically to reagents and methods for accomplishing multiplex image analysis of chromosomes and chromosomal fragments. The invention may be used to diagnose chromosomal abnormalities, infectious agents, etc.

BACKGROUND OF THE INVENTION

The determination of the presence and condition of chromosomes and chromosomal fragments in a biological sample is of immense importance in the diagnosis of disease. Traditionally, such determinations have been done manually by inspecting metaphase chromosomal preparations that have been treated with specialized stains to reveal characteristic banding patterns. Unfortunately, the interpretation of such banding patterns requires substantial skill and is technically difficult. Hence, alternate methods of analyzing chromosomal presence and arrangement have been sought.

One alternative approach to the problem of chromosome identification has involved the use of labeled chromosome-specific oligonucleotide probes to label repetitive sequences of interphase chromosomes (Cremer, T. et al., *Hum. Genet.* 74:346–352 (1986); Cremer, T. et al., *Exper. Cell Res.* 176:119–220 (1988)). Such methods have been shown to be useful in the prenatal diagnosis X Down's Syndrome, as well as in the detection of chromosomal abnormalities associated with tumor cell lines. Chromosome-specific probes of repetitive DNA that localize to discrete sub-regions of a chromosome are, however, unsuitable for analyses of many types of chromosomal abnormalities (e.g., translocations or deletions).

Ward, D. C. et al. (PCT Application WO/05789, herein incorporated by reference) discloses a chromosomal in situ suppression ("CISS") hybridization method for specifically labeling selected mammalian chromosomes in a manner that permits the recognition of chromosomal aberrations. In that method, sample DNA is denatured and permitted to hybridize with a mixture of fluorescently labeled chromosome-specific probes having high genetic complexity and unlabeled non-specific competitor probes. Chromosomal images were obtained as described by Manuelidis, L. et al. (*Chromosoma* 96:397–410 (1988), herein incorporated by reference). The method provides a rapid and highly specific assessment of individual mammalian chromosomes. The method permits, by judicious selection of appropriate probes and/or labels, the visualization of sub-regions of some or all of the chromosomes in a preparation. For example, by using more than one probe, each specific for a sub-region of a target chromosome, the method permits the simultaneous analysis of several sub-regions on that chromosome. The number of available fluorophores limits the number of chromosomes or chromosomal sub-regions that can be simultaneously visualized.

As described in PCT Application WO/05789, a "combinatorial" variation of the CISS method can be employed. In the simplest case, two fluors permit three different chromosomes or chromosomal sub-regions to be simultaneously visualized. In this variation, a hybridization probe mixture is made from a single set of probe sequences composed of two halves, each separately labeled with a different fluorophore. Upon hybridization, the two fluorophores produce a third fluorescence signal that is optically distinguishable from the color of the individual fluorophores. Extension of this approach to Boolean combinations of n fluorophores permits the labeling of $2^n-1$ chromosomes.

Ried, T. et al. (*Proc. Natl. Acad. Sci. (U.S.A.)* 89:1388–1392 (1992), herein incorporated by reference) describes the use of an epi-fluorescent microscope equipped with a digital imaging camera and computer software to "pseudocolor" the fluorescence patterns obtained from simultaneous in situ hybridization with seven probes using three fluorophores. The use of wavelength-selective filters allows one to isolate and collect separate gray scale images of each fluorophore. These images can be subsequently merged via appropriate software. The sensitivity and linearity of CCD cameras surmounts the technical difficulties inherent in color film-based photomicroscopy.

Although such efforts have increased the number of chromosomes that can be simultaneously detected and analyzed using in situ hybridization methods, it would be highly desirable to define a set of fluorophores having distinguishable emission spectra to permit the simultaneous detection and analysis of large numbers of different chromosomes and chromosomal sub-regions. The present invention provides such reagents as well as methods and apparatus for their use.

SUMMARY OF THE INVENTION

The invention concerns reagents and methods for combinatorial labeling of nucleic acid probes sufficient to permit the visualization and simultaneous identification of all 22 autosomal human chromosomes and the human X and Y chromosomes, or defined sub-regions thereof. Such specific labeling of entire chromosomes or defined sub-regions thereof is referred to as "painting."

In detail, the invention provides a method of simultaneously identifying and distinguishing the individual autosomal and sex chromosomes of a human karyotype which comprises the steps:

(a) contacting a preparation of the chromosomes, in single-stranded form, under conditions sufficient to permit nucleic acid hybridization to occur with a set of combinatorially labeled oligonucleotide probes, each member thereof: (i) having a predetermined label distinguishable from the label of any other member of the set, and (ii) being capable of specifically hybridizing with one predetermined autosomal or sex chromosome of a human karyotype; the set having sufficient members to be capable of specifically hybridizing each autosomal or sex chromosome of the human karyotype to at least one member, and so as to particulatly permit the distinguishable labeling of each autosomal or sex chromosome of the human karyotype so labeled.; wherein the contacting thereby causes at least one of each autosomal or sex chromosome of the preparation to become hybridized to at least one member of the set of probes;

(b) for each chromosome of the preparation hybridized to a member of the set of probes, employing an interferometer (preferably a common path interferometer, and most preferably a Sagnac common path interferometer) to detect and identify the predetermined label of that member and correlating the identity of the label of that member with the identity of the autosomal or sex chromosome of the human karyotype with which that member specifically hybridizes, to thereby identify the chromosome hybridized to the member; and (c) repeating step (b) until each autosomal and sex chromosome of the human karyotype has been identified in the preparation.

The invention also concerns the embodiment of the above method, wherein, in step (b), an interferogram is produced from the interferometer, and the interferogram is Fourier transformed to recover the spectral signature of the predetermined label of the hybridized probe member, and more preferably, wherein the spectral signature of the predetermined label of the hybridized probe member in step (b) is recovered by comparing the interferogram to a library or lookup table of previously determined interferograms.

The invention also concerns an interferometer (preferably a common path interferometer, and most preferably a Sagnac common path interferometer) that simultaneously identifies and distinguishes the individual autosomal and sex chromosomes of a human karyotype which comprises means for:

(a) incubating a preparation of the chromosomes, in single-stranded form, under conditions sufficient to permit nucleic acid hybridization to occur with a set of combinatorially labeled oligonucleotide probes, each member thereof: (i) having a predetermined label distinguishable from the label of any other member of the set, and (ii) being capable of specifically hybridizing with one predetermined autosomal or sex chromosome of a human karyotype; the set having sufficient members to be capable of specifically hybridizing each autosomal or sex chromosome of the human karyotype to at least one member; wherein the contacting thereby causes at least one of each autosomal or sex chromosome of the preparation to become hybridized to at least one member of the set of probes;

(b) detecting and identifying, for each chromosome of the preparation hybridized to a member of the set of probes, the predetermined label of that member and correlating the identity of the label of that member with the identity of the autosomal or sex chromosome of the human karyotype with which that member specifically hybridizes, to thereby identify the chromosome hybridized to the member; and (c) repeating steps (b) and (c) until each autosomal and sex chromosome of the human karyotype has been identified in the preparation.

The invention also provides such an interferometer, wherein, in step (b), an interferogram is produced from the interferometer, and the interferogram is Fourier transformed to recover the spectral signature of the predetermined label of the hybridized probe member, and more preferably, wherein the spectral signature of the predetermined label of the hybridized probe member in step (b) is recovered by comparing the interferogram to a library or lookup table of previously determined interferograms.

BRIEF DESCRIPTION OF THE FIGURES

The file of this patent contains at least one drawing executed in color copies of this patent with color drawing's will be provided by the Patent and Trademark Office upon request and payment of the neccessary fee.

In FIG. 2, panels A and B are the DAPI image and mask; panels C and D are FITC image and mask; panels E and F are Cy3 image and mask; panels G and H are Cy3.5 image and mask; panels I and J are Cy5 image and mask; and panels K and L are Cy7 image and mask.

FIG. 2 is the same photograph as FIG. 3A, except that it is gray scale pseudocolored. FIG. 3B displays the karyotypic array of the chromosomes.

DESCRIPTION OF THE PREFERRED EMBODIMENTS

A. Overview of the Invention

Figure 1:
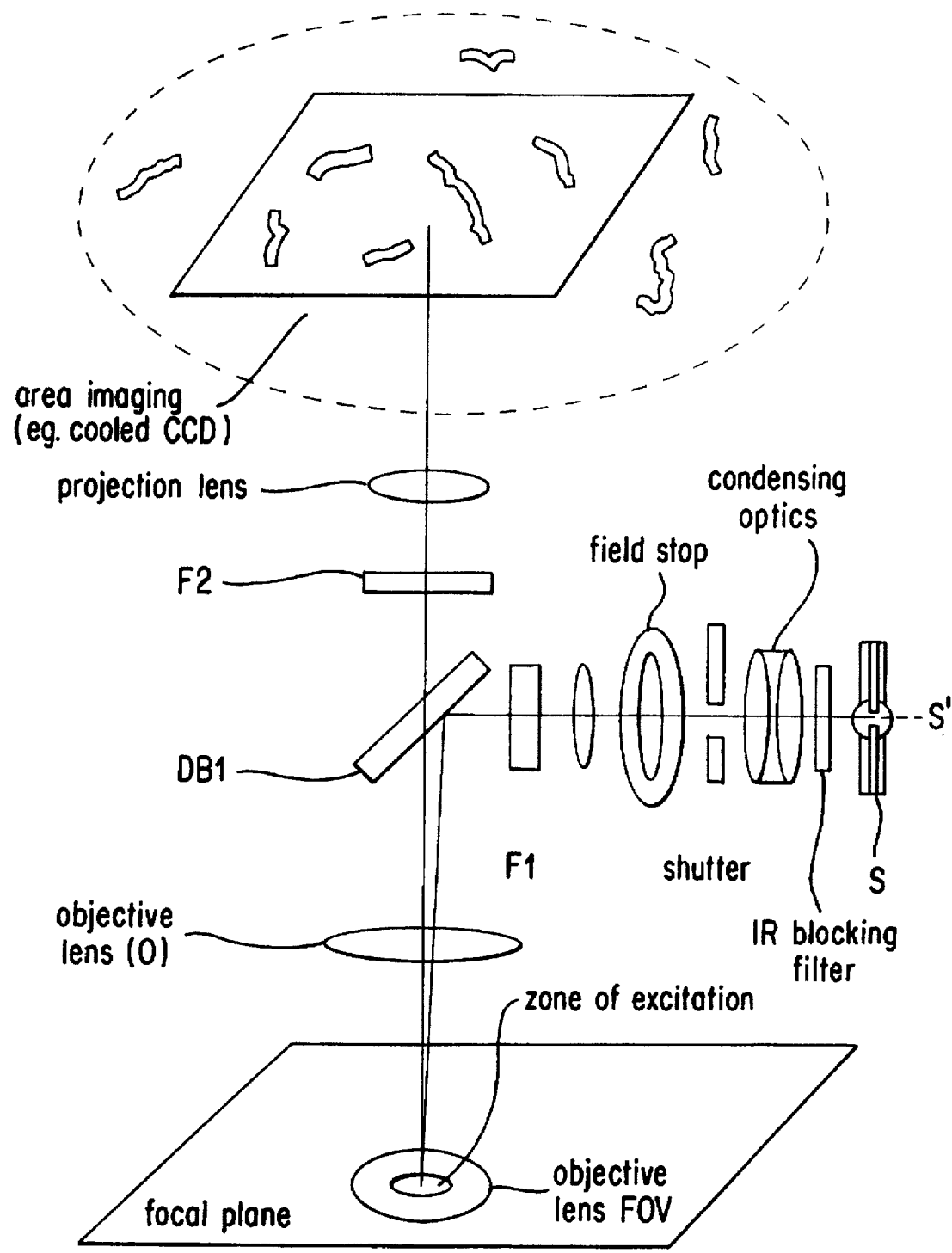
FIG. 1 provides a schematic illustration of a CCD camera and microscope employed in accordance with the present methods.
Figure 2A:
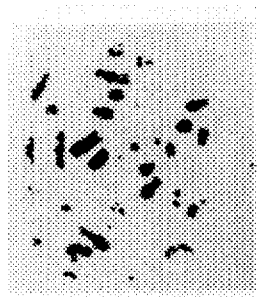
FIG. 2 shows the raw data from a karyotypic analysis of chromosomes from a bone marrow patient (BM2486). Adjacent to each source image is a chromosome "mask" generated by the software program.
Figure 2B:
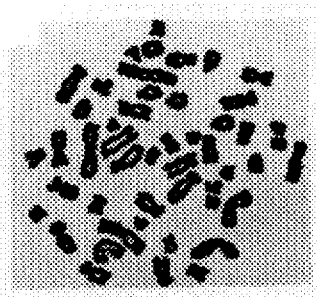
Figure 2C:
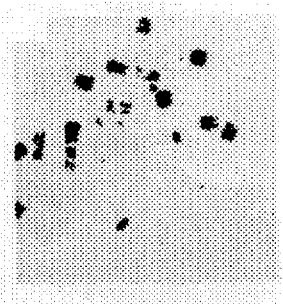
Figure 2D:
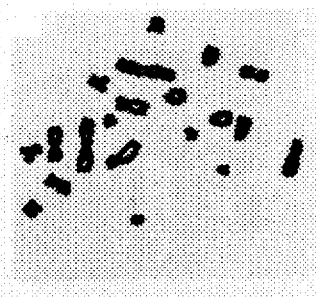
Figure 2E:
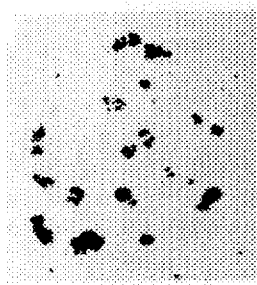
Figure 2F:
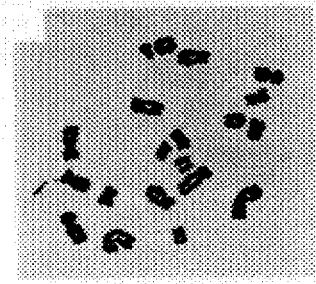
Figure 2G:
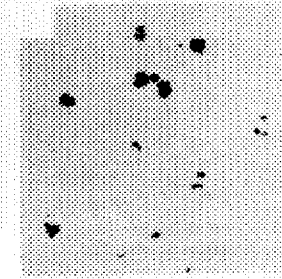
Figure 2H:
Figure 2I:
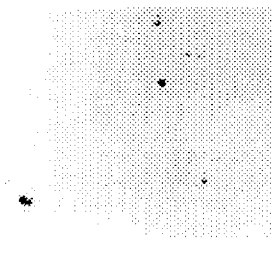
Figure 2J:
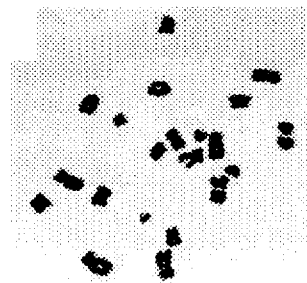
Figure 2K:
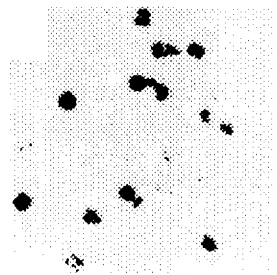
Figure 2L:
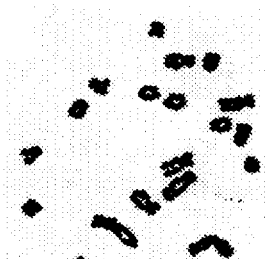

Fluorescence in situ hybridization (FISH) is used in a variety of areas of research and clinical diagnostics (Gray, J. W. et al., Curr Opin Biotech 3:623–631 (1992); Xing, Y. et al., In: The Causes and Consequences of Chromosomal Aberrations. I. R. Kirsch Ed. CRC Press, Boca Raton, pages 3–28 (1993)). For the study of the chromosomal and suprachromosomal organization of the cell nucleus it is an indispensable tool (Cremer, T. et al., In: Cold Spring Harbor Symposia on Quantitative Biology, Volume LVIII, pp. 777–792, Cold Spring Harbor Laboratory Press, NY (1994)). Most importantly FISH offers the capacity for multiparameter discrimination. This allows the simultaneous visualization of several DNA probes using either a combinatorial (Nederlof, P. M. et al., Cytometry 10:20–27 (1989); Nederlof, P. M. et al., Cytometry 11:126–131 (1990); Ried, T. et al., Proc Natl Acad Sci (U.S.A.) 89:1388–1392 (1992a); Ried, T. et al., Hum Mol Genet 1:307–313 (1992b); Lengauer, C. et al., Hum Mol Genet 2:505–512 (1993); Popp, S. et al., Human Genetics 92:527–532 (1993); Wiegant, J. et al., Cytogenet Cell Genet 63:73–76 (1993)) or a ratio labeling (Dauwerse, J. G. et al., Hum Mol Genet 1:593–598(1992); Nederlof, P. M. et al., Cytometry 13:839–845 (1992); du Manoir, S. et al., Hum Genet 90:590–610 (1993)) strategy. Up to twelve DNA probes have been visualized (Dauwerse, J. G. et al., Hum Mol Genet 1:593–598 (1992)). Consequently, the goal of 24 different colors has long been sought (Ledbetter, D. H., Hum Mol Genet 5:297–299 (1992)). Twenty-four different colors are an important threshold because they would allow the simultaneous visualization of the 22 autosomes and both sex chromosomes. Beside improved karyotyping, the possibility of simultaneously hybridizing 24 different and distinguishable DNA probes would allow the addressing of a large number of important biological questions. However, the previously published multicolor systems lacked the versatility for an extension to 24 colors and only proof-of-principle experiments were ever published.

The present invention results, in part, from the realization of multiparametric fluorescence in situ hybridization to achieve the simultaneous visualization of 24 different genetic targets with a combinatorial labeling strategy. This strategy permits discrimination between many more target sequences than there are spectrally distinguishable labels. The simplest way to implement such labeling is using a simple "Boolean" combination, i.e., a fluor is either completely absent (i.e. the value of "0" will be assigned) or present in unit amount (value of 1). For a single fluor A, there is only one useful combination (A=1) and for two fluors A and B, there are 3 useful combinations (A=1/B=0; A=0/B=1; A=1/B=1). There are 7 combinations of 3 fluors, 15 combinations of 4 fluors, 31 combinations of 5 fluors, 63 combinations of 6 fluors, and so on (fluorophores permitting the labeling of $2^n 1$ chromosomes). Thus, to uniquely identify all 24 chromosome types in the human genome using chromosome painting probe sets, only 5 distinguishable fluors are needed (31 total combinations). If each probe set is labeled with one or more of five spectrally distinct fluorophores in a combinatorial fashion, simple Boolean combination can be used to identify each DNA probe by a spectral signature dictated by its fluorophore composition.

B. Terminology of the Invention

The invention concerns a set of combinatorially labeled oligonucleotide probes, each member thereof: (i) having a predetermined label distinguishable from the label of any other member of the set, and (ii) being capable of specifically hybridizing with one predetermined autosomal or sex chromosome of a human karyotype. In the most preferred embodiment, the set will have a sufficient number of members to be capable of specifically and distinguishably hybridizing each autosomal or sex chromosome of said human karyotype to at least one member. As used herein, the term "karyotype" denotes the compliment of chromosomes found in a normal or aberrant cell. In a normal cells, the number of chromosomes is 46, comprising 22 pairs of autosomal chromosomes and 2 sex chromosomes (either 2 X chromosomes (if female) or an X and Y chromosome (if male)). The labels are said to be distinguishable in that the particular label of any one member of the set (and the identity of that member) differ from the particular label and identity of any other member of the set. Since each probe member is capable of specifically hybridizing to only one chromosome (or sub-chromosomal region) and since the identity of the label and probe are known in advance, the detection of a particular label associated with an unidentified chromosomal region means that the probe bearing that label has become hybridized to the unidentified chromosomal region. Since the chromosome to which that probe specifically hybridizes is known, the detection of a distinguishable label permits the identification of the chromosomal region.

More specifically, the invention concerns fluors that can be used to label oligonucleotide probes so that such probes may be used in multiparametric fluorescence in situ hybridization. As used herein, a "fluor" or "fluorophore" is a reagent capable of emitting a detectable fluorescent signal upon excitation. In a preferred embodiment, the fluor is conjugated to a ligand capable of binding to a modified nucleotide residue. The most preferred ligands for this purpose are avidin, streptavidin, biotin-binding antibodies and digoxigeninbinding antibodies. Methods for performing such conjugation are described by Pinkel, D. et al., *Proc. Nat'l. Acad. Sci. (U.S.A.)* 83:2934–2938 (1986), herein incorporated by reference). Alternatively, the fluor may be coupled directly to the pyrimidine or purine ring of the nucleotides of the probe (Ried, T. et al. (*Proc. Natl. Acad. Sci. (U.S.A.)* 89:1388–1392 (1992), herein incorporated by reference; U.S. Pat. Nos. 4,687,732; 4,711,955; 5,328,824; and 5,449,767, each herein incorporated by reference.

The term "multiparametric fluorescence" denotes the combinatorial use of multiple fluors to simultaneously label the same chromosome or sub-chromosomal fragment, and their detection and characterization. Chromosomes or sub-chromosomal fragments are said to be simultaneously labeled if they are exposed to more than a single chromosome-specific probe under conditions sufficient to permit each chromosome-specific probe to independently hybridize to its target chromosome. As used herein, it is thus unnecessary for all such hybridization reactions to commence and conclude at the same instant. The simultaneous labeling permitted by the present invention is thus in contrast to protocols in which chromosomes are exposed to only a single chromosome-specific probe at a time.

The simultaneous detection and characterization permitted by the present invention denotes an ability to detect multiple (and most preferably all) of the autosomal and/or sex chromosomes in a sample, without any need to add further reagent, or probe after the detection of the first chromosome.

In the simplest embodiment, digital images of the chromosomes are obtained for each fluorophore employed, thereby providing a series of gray scale fluorescence intensities associated with each fluorophore and each chromosome. The final image is obtained by pseudocoloring the blended gray scale intensities for each chromosome.

The invention thus provides a method of simultaneously identifying and distinguishing the individual autosomal and sex chromosomes of a human karyotype which comprises contacting a preparation of chromosomes, that has been previously treated to render it in single-stranded form, with the above-described set of combinatorially labeled oligonucleotide probes, under conditions sufficient to permit nucleic acid hybridization to occur.

Such treatment causes at least one of each autosomal or sex chromosome of the preparation to become hybridized to at least one member of said set of probes. For each chromosome of the preparation hybridized to a member of the set of probes one next detects and identifies the predetermined label of that member and correlates the identity of the label of that member with the identity of the autosomal or sex chromosome of said human karyotype with which that member specifically hybridizes. This process identifies the chromosome hybridized to the member. This last step is repeated until each or a desired number of autosomal and sex chromosome of the human karyotype has been identified in the preparation.

The oligonucleotide probes used in accordance with the methods of the present invention are of either of two general characteristics. In one embodiment, such probes are chromosome or sub-chromosome specific (i.e., they hybridize to DNA of a particular chromosome at lower $c_o t^{1/2}$ than with DNA of other chromosomes; $c_o t^{1/2}$ being the time required for one half of an initial concentration ($c_o$) of probe to hybridize to its complement). Alternatively, such probes are feature (e.g., telomere, centromere, etc.) specific. Both types of probes may be used if desired. Sources of such probes are available from the American Type Culture Collection, and similar depositories.

The oligonucleotide probes used in accordance with the methods of the present invention are of a size sufficient to permit probe penetration and to optimize reannealing hybridization. In general, labeled DNA fragments smaller than 500 nucleotides in length, and more preferably of approximately 150–250 nucleotides in length, probes are employed. Probes of such length can be made by synthetic or semi-synthetic means, or can be obtained from longer polynucleotides using restriction endonucleases or other techniques suitable for fragmenting DNA molecules. Alternatively, longer probes (such as polynucleotides) may be employed.

Most preferably, the oligonucleotide probes are synthesized so as to contain biotinylated or otherwise modified nucleotide residues. Methods for accomplishing such biotinylation or modification are described in U.S. Pat. Nos. 4,687,732; 4,711,955; 5,328,824; and 5,449,767, each herein incorporated by reference. Biotinylated nucleotides and probes are obtainable from Enzo Biochem, Boehringer Mannheim, Amersham and other companies. In brief, such biotinylated or otherwise modified nucleotides are produced by reacting a nucleoside or nucleotide with a mercuric salt under conditions sufficient to form a mercurated nucleoside or nucleotide derivative. The mercurated product is then reacted in the presence of a palladium catalyst with a moiety (e.g., a biotin group) having a reactive terminal group and comprising three or more carbon atoms. This reaction adds the moiety to the purine or pyrimidine ring of the nucleoside or nucleotide.

In a highly preferred embodiment, such modified probes are used in conjunction with competitor DNA in the manner described by Ward et al. (WO90/05789), herein incorporated by reference. Competitor DNA is DNA that acts to suppress hybridization signals from ubiquitous repeated sequences present in human and other mammalian DNAs. In the case of human DNA, alu or kpn fragments can be employed, as described by Ward et al. (WO90/05789). Initially, probe DNA bearing a detectable label and competitor DNA are combined under conditions sufficient to permit hybridization to occur between molecules having complementary sequences. As used herein, two sequences are said to be able to hybridize to one another if they are complementary and are thus capable of forming a stable antiparallel double-stranded nucleic acid structure. Conditions of nucleic acid hybridization suitable for forming such double stranded structures are described by Maniatis, T., et al. (In: *Molecular Cloning, A Laboratory Manual*, Cold Spring Harbor Laboratories, Cold Spring Harbor, N.Y. (1982)), by Haymes, B. D., et al. (In: *Nucleic Acid Hybridization, A Practical Approach*, IRL Press, Washington, D.C. (1985), and by Ried, T. et al. (*Proc. Natl. Acad. Sci. (U.S.A.)* 89:1388–1392 (1992)). For the purpose of the present invention, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization and formation of a double-stranded structure.

The quantity of probe DNA combined with competitor DNA is adjusted to reflect the relative DNA content of the chromosome target. For example, as disclosed by Ward et al. (WO90/05789), chromosome 1 contains approximately 5.3 times as much DNA as is present in chromosome 21. Thus, a proportionally higher probe concentration would be employed when using chromosome 1 specific probes.

The resulting hybridization mixture is then treated (e.g., by heating) to denature the DNA present and is incubated at approximately 37° C. for a time sufficient to promote partial reannealing. The sample containing chromosomal DNA to be identified is also heated to render it susceptible to being hybridized to the probe. The hybridization mixture and the sample are then combined, under conditions sufficient to permit hybridization to occur. Thereafter, the detection and analysis of the hybridized product is conducted by detecting the fluorophore label of the probe in any of the methods described below.

In an alternative embodiment, a modification of the method of Ried T. et al. (*Proc. Natl. Acad. Sci. (U.S.A.)* 89:1388–1392 (1992), herein incorporated by reference) is employed. Thus, probes are labeled with biotinylated nucleotides, and permitted to hybridize to chromosomal DNA. After hybridization, the hybridized complexes are incubated in the presence of streptavidin, that had been conjugated to one or more fluors. The streptavidin binds to the biotinylated probe of the hybridized complex thereby permitting detection of the complex, as described below.

C. The Preferred Fluorophores of the Invention

By labeling with two or more fluors in combination, it is possible to discriminate between many more objects than there are available fluors. The simplest way to implement such labeling is by Boolean combination, i.e., a fluor is either completely absent (0) or present in unit amount (1). For a single fluor A, there is only one useful combination (A=1). For two fluors A, B there are 3 useful combinations (A=1, B=0; A=0, B=1; A=1, B=1). For three fluors A, B, C, there are 7 combinations (A=1, B=0, C=0; A=0, B=1, C=0; A=0, B=0, C=1; A=1, B=1, C=0; A=1, B=0, C=1; A=0, B=1, C=1; A=1, B=1, C=1). There are 15 combinations of 4 fluors, 31 combinations of 5 fluors, 63 combinations of 6 fluors, and so on.

To uniquely code all 24 chromosome types in the human genome, 5 distinguishable combinatorial fluors are needed. With a 5-fluor set, 15 chromosomes can be distinguished using combinations of 4 of the 5 fluors. The labeling of the remaining 9 chromosomes requires all five fluors to be used combinatorially. Seven of the available 5-fluor combinations are not required. Thus, there is a certain amount of latitude available to avoid any 5-fluor combination that might prove particularly hard to resolve. In particular, quaternary or quinternary combinations may be avoided.

One aspect of the present invention concerns the identification of a set of seven fluors that are be well resolvable by the excitation-emission contrast (EEC) method.

As indicated above, multi-fluor combinatorial labeling depends in general on acquiring and analyzing the spectral signature of each object i.e., obtaining the relative weighting coefficients of the component fluors. Because full spectroscopic analysis of mixed fluor spectra (e.g., by interferometry) is not yet sufficiently developed, the method chosen was conventional bandwidth-restricted widefield imaging using epi-fluorescence triplets, viz. excitation filter, dichroic reflector and emission bandpass filter. The limited spectral bandwidth available for imaging (roughly 380–750 nm), and the extensive overlap between the spectra of organic fluors, makes separating multiple fluors spectroscopically during the imaging step a significant technical challenge.

To make software segmentation of the source images as straightforward as practicably possible, a target figure of <10% crosstalk between any given fluor and the two adjacent channels was set. Computer modeling indicated that for DAPI plus the five combinatorial fluors FITC, Cy3, Cy3.5, Cy5, Cy5.5, this level of contrast cannot be attained using either excitation selection or emission selection alone, no matter how narrow the filter bandwidths. Thus, both excitation selection and emission selection must be invoked simultaneously. This is referred to as excitation-emission contrast (EEC).

Contrast ratio plots were first computed for each of the fluors vs. its two neighbors. These plots indicate regions where pairwise contrast is high enough to be useful. A constraint on the practically attainable contrast is that regions of high contrast generally lie far down the flanks of at least one of the spectra i.e., where excitation and/or emission are strongly sub-optimum. Further, to attain the required degree of selectivity it is necessary to use filters of bandwidths in the range 5–15 nm (cf. approx. 50 nm for 'standard' filter sets). Together, these impose a severe sensitivity penalty. The goal of 10% maximum crosstalk represents an acceptable, practical compromise between sensitivity and selectivity.

A fundamental asymmetry exists between excitation contrast and emission contrast. For low-noise detectors such as the cooled CCD, restricting the excitation bandwidth has little effect on attainable image S/N ratio; the only penalty is the need for longer exposure times. Restricting the emission bandwidth is very undesirable, however, since every fluorescence photon blocked by the filter represents irreversible photochemical bleaching of the fluor. For this reason, the highest practicable contrast was invoked on the excitation side. A suitable emission filter was then found to give the necessary EEC ratios. Filter selection is additionally constrained by the fact that each channel must adequately reject both adjacent channels simultaneously: improving one may significantly degrade the other. Good contrast was attainable in practice for all fluors except the Cy5.5/Cy5 pair, which is marginal. For this reason, Cy7 was later substituted for Cy5.5. Other considerations relating to choice of filters include:

1. Commercial narrow-band interference filters may have a large amount of wedging i.e., non-parallelism between the top and bottom faces. This results in large image shifts (up to several microns equivalent). The shift is a vector characteristic of each filter and its orientation in the epicube. Thus, automatic compensation for image displacement is a necessary part of the processing software.
2. Manufacturing variations of a few nm in peak wavelength and FWHM specifications can have significant effects on the EEC ratios. Filter errors to long wavelength may be fine-tuned by tilting, but this option is severely curtailed in the case of emission filters because of increased image aberrations and worsened pixel shifts. There is no equivalent way to compensate short-wavelength errors.
3. the need to prevent infra-red light emitted by the arc lamp from reaching the detector. Silicon CCD's are extremely sensitive in this region. Filter sets for the blue and midvisible fluors were found not to need additional IR blocking, but loss of image contrast due to spurious IR was found to be a serious problem for the red—far red—near IR fluors. Heat filters routinely used in microscopy (e.g., Schott BG-38 glass) are completely inadequate to alleviate this problem. Thus, extensive additional blocking was required. However, available commercial interference filters for infra-red blocking filters also transmit poorly in the near UV, and thus cannot be inserted in the excitation path. Instead, it was found necessary to put the IR blocking filters into the emission path. To minimize loss of image quality by insertion of these filters in the image path, they are placed inside the CCD camera, immediately in front of the window. In practice, two interchangeable filters were chosen, one for use with Cy5, Cy5.5 (Oriel #58893; 740 nm cutoff) and one for use with Cy7 (Oriel 58895; 790 nm cutoff).

The first member of the set of fluors is the counterstain DAPI, which gives a weak G-like banding pattern. Five of the remaining six fluors may be used combinatorially to paint the entire human chromosome set. All are available as avidin conjugates (for secondary detection of biotinylated probe libraries) or directly linked to dUTP (for direct labeling).

Thus, a set of six fluors and corresponding optical filters spaced across the spectral interval 350–750 nm was identified that achieve a high discrimination between all possible fluor pairs. These fluors comprise the preferred fluors of the present invention and are: 4'-6-diamidino 2-phenyl indole (DAPI), fluorescein (FITC), and the new generation cyanine dyes Cy3, Cy3.5, Cy5, Cy5.5 and Cy7. Of these Cy3, Cy3.5, Cy5 and Cy7 are particularly preferred, The absorption and emission maxima for the respective fluors are: DAPI (Absorption maximum: 350 nm; Emission maximum: 456 nm), FITC (Absorption maximum: 490 nm; Emission maximum: 520 nm), Cy3 (Absorption maximum: 554 nm; Emission maximum: 568 nm), Cy3.5 (Absorption maximum: 581 nm; Emission maximum: 588 nm), Cy5 (Absorption maximum: 652 nm; Emission maximum: 672 nm), Cy7 (Absorption maximum: 755 nm; Emission maximum: 778 nm). Complete properties of selected fluorescent labeling reagents are provided by Waggoner, A. (*Methods in Enzymology* 246:362–373 (1995) herein incorporated by reference).

D. Methods for the Detection of Fluorescent In Situ Hybridization

1. The Theory of Fluorescence Detection

Of the various methods for contrast generation in site-specific labeling, fluorescence is arguably the most powerful, because of its high absolute sensitivity and multiparameter discrimination capability. Modem electronic cameras used in combination with high numerical aperture microscope objectives and state of the art optical filters are capable of imaging structures labeled with as little as a 10–100 fluor molecules per pixel. Thus, fluor-tagged single-copy DNA sequences as small as a few hundred bases in size are detectable under favorable conditions. The availability of families of spectrally distinguishable fluors makes simultaneous imaging of several different targets in the same specimen possible, either directly or through combinatorial or analog multiplex methods. In principle, multi-fluor discrimination may be based on differential excitation of the fluors, differential emission, fluorescence lifetime differences, or on more complex but still analyzable observables such as fluorescence anisotropy. This discussion assumes an epi-imaging geometry. Table 1 describes the symbols and operators relevant to the theoretical considerations of fluorescence.

TABLE 1

| Instrument Parameter | Units | Definition |
|---|---|---|
| $\psi_s(\lambda)$ | photon s$^{-1}$nm$^{-1}$ | spectral distribution of source, assumed to be an isotropic radiator over $4\pi$ steradians |
| $\phi_s$ | dimensionless | collection of efficiency of condenser optics |
| $\psi 1(\lambda)$ | photon s$^{-1}$m$^{-2}$nm$^{-1}$ | spectral distribution of photons in collimated beam of excitation light impinging on excitation filter F1 |
| $f1(\lambda)$ | dimensionless | transmittance function of excitation filter F1 |
| $\psi 2(\lambda)$ | photon s$^{-1}$cm$^{-2}$nm$^{-1}$ | spectral distribution of photons in collimated beam of excitation light emerging from F1 and impinging on dichroic beamsplitter DB1 |
| $R(\lambda)$ | dimensionless | reflectance function of dichroic beamsplitter DB1 |
| $T(\lambda)$ | dimensionless | transmittance function of dichroic beamsplitter DB1 |
| $\psi 3(\lambda)$ | photon s$^{-1}$cm$^{-2}$nm$^{-1}$ | spectral distribution of photons in collimated beam of fluorescence emerging from DB1 and impinging on emission filter F2 |
| $f2(\lambda)$ | dimensionless | transmittance function of emission filter F2 |
| $\psi 4(\lambda)$ | photon s$^{-1}$cm$^{-2}$nm$^{-1}$ | spectral distribution of photons in collimated beam of excitation light emerging from F2 and entering the entrance pupil of the objective lens |
| $\mu$ | dimensionless | linear magnification factor of objective lens |
| $\psi 5(\lambda)$ | photon s$^{-1}$cm$^{-2}$nm$^{-1}$ | spectral distribution of photons in focused beam of excitation light traversing the specimen plane |
| $\phi d(\lambda)$ | dimensionless | quantum efficiency of detector |
| $\Omega$ | pixel.$\mu^{-1}$ | magnification factor of final image at detector |
| $\epsilon(\lambda)$ | M$^{-1}$cm$^{-1}$ | molar decadic extinction coefficient of fluor $F_a$. |

TABLE 1-continued

| Instrument Parameter | Units | Definition |
|---|---|---|
| τ | s | decay lifetime of excited state of fluor $F_a$. |
| $\sigma_{Fa}(\lambda)$ | $cm^{-1}$ | photon absorption cross-section of fluor $F_a$. |
| φFa | dimensionless | fluorescence quantum efficiency of fluor $F_a$. |
| $f_a(\lambda)$ | dimensionless | normalized spectral distribution of fluorescence from fluor $F_a$. |

Whether a given excitation rate at pixel location p will give an acceptable fluorescence signal/noise ratio (defined as S/N =[signal mean]/[variance due to all noise sources]) in a given integration period depends on the number of fluor molecules within p, their quantum yield and photochemical stability, and the quantum efficiency and noise performance of the detector.

In the limit of weak excitation ($\psi^{(\lambda)}.\sigma_F^{(\lambda)} << \tau^{-1}$), the rate of excitation of the N molecules of fluor F within pixel p in object space is:

$$R(p) = N \int_{i\psi} {}^{S(\lambda,p)}.\sigma_F^{(\lambda)}.d\lambda s^{-1}$$

$_\psi S(\lambda)$ is the spectral distribution of exciting light passing through the focal plane of the microscope (photon $nm^{-1}$. $cm^{-2}.s^{-1}$). It is approximately given by $\psi_s^{(\lambda)}.\phi_s.f1(\lambda).R(\lambda) .\alpha^2.\mu$, where α=diameter of objective lens entry pupil/ diameter of collimated beam from condenser. The integral is taken over the bandwidth (i) for which the fluor has non-zero absorption cross section $\sigma_F^{(\lambda)}$, which is related to the molar decadic extinction coefficient $\epsilon_F(\lambda)$ by the expression:

$$\sigma_F^{(\lambda)} = 3.825 \times 10^{-21} \epsilon_F(\lambda) cm^2.$$

In practice, $\int_i \psi^{S(\lambda,p)}. d\lambda$ can be measured with a bolometric detector such as a calibrated micro-thermopile placed at or near the focal plane of the objective lens.

For a perfectly noiseless detector and a non-bleachable fluor, the S/N of each pixel increases indefinitely as (photons detected)$^{1/2}$. How rapidly S/N increases depends on excitation strength, but the relationship between S/N and dose does not. The effect of non-zero bleaching constant is to change the $t^{1/2}$ function to an asymptotic function, the form of which depends on the bleaching mechanism. However, because the bleaching rate and the signal strength are linearly related, the asymptote once again does not depend at all on excitation rate, although the speed of approach to the asymptote does. If finite camera noise is added to photobleaching, it is found that the S/N climbs to a maximum value, then falls as the fluor is exhausted. Now both the kinetics and the peak S/N depend of excitation rate, in general the faster the excitation the higher the maximum attainable S/N. However, for contemporary cooled CCD cameras the dark noise is so low that it can be virtually ignored on the timescale of bleaching (typically a few minutes); a more important factor in determining ultimate S/N is the stray light background (esp. from nonspecific luminescences and leakage of excitation light).

Note that although the microscope objective compresses the excitation beam, in a nonconfocal microscope it does not focus it to a point and so has no bearing on the fluorescence image resolving power (incoherent emitter).

The commonest excitation source for fluorescence microscopy is the high pressure short mercury arc, whose spectrum consists of pressure-broadened lines from the UV to the middle region of the visible spectrum (principal wavelengths are 334.1 nm, 365.6 nm, 404.7 nm, 435.8 nm, 546.1 nm, 577.9 nm), superimposed on a weaker thermal continuum. Many fluorophores have excitation spectra that overlap one or other of the mercury lines to an acceptable extent. Others (of which the best known is FITC) do not, but may be adequately excited by the continuum if a wide enough excitation bandwidth is employed. Another common source is the high pressure xenon short arc, which produces an almost uniform continuum from ca. 300 nm: to beyond 900 nm. However, the power $nm^{-1}$, is almost everywhere less than the mercury continuum for the same arc wattage. If high intensity light with no structure is required (e.g., for fluorescence ratio imaging) a high CW power or pulsed quartz halogen lamp outperforms the xenon beyond about 450 nm. Certain fluors are well matched to laser excitation (e.g., Ar+@488 nm for FITC, He-Ne @632.8 nm for Cy5, semiconductor diode—pumped YAG @680 nm for Cy5.5).

In single-fluor imaging, use of the available spectral bandwidth is rarely stringent. The excitation filter F1 and dichroic beamsplitter DB1 can usually be chosen to give adequate overlap between the source spectrum and the fluor excitation spectrum. If an arc line is available, the F1 bandpass need be no wider than the line. If not, and part of the thermal continuum must be used, the wider the F1 bandpass the greater will be the available excitation flux. However, with low noise integrating detectors the goal of high excitation efficiency is generally secondary to the need to exclude excitation light from the emission path. This limits how close the excitation and emission bandpasses can be placed to one another, and hence constrains the excitation bandwidth. For fluors with small Stokes' shifts, high quality filters with very steep skirts are required. The excitation filter must be rigorously 'blocked' on the long wavelength side, and have no pinholes, scratches, or light leaks around the edge.

Dichroic beamsplitters are currently much less 'evolved' than bandpass interference filters, meaning that the slopes of their transmit <--> reflect transitions are far less than the skirt slopes of premium notch filters, and there may be large spectral intervals where they oscillate between intermediate states of partial reflectance and transmittance. The main purpose of a dichroic beamsplitter is to improve the combined efficiency of excitation and emission, rather than to define the wavelength response of the instrument.

The resolvability of overlapping fluors in imaging microscopy may depend critically on the degree of excitation contrast that can be achieved (see C, below). The variation with wavelength of the ratio of the extinction coefficient of two fluors is the excitation contrast spectrum. It can readily be calculated from the digitized absorption spectra. Depending on the overlap of the absorptions, their ratio spectrum may either show a distinct peak or may grow indefinitely large. In either case, it is usually possible to choose an excitation wavelength that favors one fluor over another to a useful extent (from a factor of 3–4 fold up to a hundredfold or more). Some difficulties in obtaining high contrast multi-fluor images include:

a. The excitation wavelengths required for high contrast imaging are often far from the absorbance peaks. Thus, there may be a high degree of intensity trade-off to obtain high signal contrast vs. other fluors.

b. From the above, standard filter sets cannot be used.

c. Arc source spectral lines t-hat are useful for exciting single fluors may not give high corast discrimination against adjacent fluors.

d. When using a broadband source or the continuum spectrum of an arc source, the need for narrow excitation bandwidth may reduce the excitation flux tc lematically low levels. It is sometimes possible to relax the constraints on excitation wavelength for the sake of more efficient excitation.

Collecting the fluorescence of F and imaging it onto the detector with high efficiency is the principal design goal of the emission optics. Operationally, it is even more important to have an efficient emission path than an efficient excitation path. The reason is that inefficient excitation causes inefficient photobleaching; the only penalty is a long image integration time (assuming a low-noise detector). On the other hand, any fluorescence lost on its way to the detector represents photobleaching without concomitant increase in the information content of the image.

The detector pixel p accumulates signal (detected photons) at a rate:

$$F(p)=G.R(p).\phi_F.\int_{ii} T(\lambda).f2(\lambda).\phi_d(\lambda).d\lambda.s^{-1}$$

The integral is over the bandwidth (ii) for which the detector quantum efficiency $\phi_d(\lambda)>0$. G represents the efficiency with which the optics gather the fluorescence and transmit it to the detector; it may be assumed to be wavelength independent to first order. The principal factor in G is the numerical aperture (NA) of the objective lens, which determines the fraction of the isotropically radiated fluorescence collected by the imaging system ($\S=1/\pi.\sin^{-1}(\theta)=1/\pi.\sin^{-1}(NA/n)$, where $\theta$ is the half-angle subtended by the objective lens from its focal point. For an oil immersion lens with NA=1.3; n=1.515; $\S=0.328$). NA additionally determines the spatial resolving power of the microscope, because it scales the dimensions of the Frauenhofer diffraction pattern produced in the image plane by a point source in the specimen plane. Several 'rules' are in use for specifying the resolving power of a lens, depending on how much overlap of the Airy discs of two adjacent objects is deemed to constitute the threshold of resolution. The commonly used Rayleigh criterion is r=1.22λ/2NA (e.g., for the above NA=1.3 lens working at 500 nm, r=0.24μ).

For a noise-free detector, image 'noise' at p is determined by the statistical variance in the number S(p) of fluorescent photons detected in time interval Δt. The only detector characteristic that has any bearing on this is its quantum efficiency $\phi d(\lambda)$.

In the absence of photobleaching (probability of destruction per hit $\Pi_b=0$), S(p)=F(p).Δt, with variance S(P)$^{1/2}$, i.e., S/N=S(p)$^{1/2}$. Image quality will therefore increase indefinitely with Δt, though at an ever decreasing rate.

In the presence of photobleaching ($\Pi_b\neq 0$), S(p) is an integral of the form:

$$S(p)=F(p)\int_{\Delta t} f(t).dt$$

where f(t) is the photobleaching decay function. S/N rises along a more or less complex path to an asymptotic value that corresponds to total exhaustion of the fluor. For the case of a unimolecular photobleaching process this would be an exponential function, i.e., $N(p,t)=N_0(1-\exp-[k_b/\Sigma k].t)$ where $k_b=\Pi_b^{-1}$ is the photobleaching constant and Σk represents all other processes by which the excited state of F is deactivated. Note that the normalized asymptote in this first-order system depends only on $k_b/\Sigma k$, and is independent of the strength of the excitation. Thus, the extent of bleaching is exponentially related to the accumulated excitation dose, but is independent of the path. In reality, however, bleaching of fluors in solution may be mechanistically and kinetically much more complex. A common mechanism involves ring opening following peroxidation of the fluor excited state, e.g., by $^1O_2$ or $O_2^{2-}$. This type of bleaching may be considerably slowed by rigorous deoxygenation or by the use of oxygen radical scavengers (i.e., antifade agents) such as tertiary amines (p-phenylene diamine or DABCO). Nevertheless, other (as yet poorly characterized) irreversible processes are not excluded, including reactions with impurities.

A nonideal detector contributes noise of many kinds, detailed analysis of which may be intractable. The simplest noise component is fluctuation in the so-called 'dark current,' i.e., the flow of thermally excited carriers within the detector. If this noise is assumed to be random, it adds to the photon shot noise in RMS fashion. Thus, if the mean photogenerated signal is F s$^{-1}$ and the mean dark count is D s$^{-1}$, the S/N after time Δt is $F.(\Delta t)^{1/2}/(F+D)^{1/2}$; S/N still increases as $(\Delta t)^{1/2}$, but more slowly than for a noiseless detector. When photobleaching is present, however, the situation is entirely different. In this case, S/N rises initially as $(\Delta t)^{1/2}$, but at some point reaches a shallow maximum and then begins to fall again, as the fluorescent signal declines but the thermal noise power remains constant. In this case, it is in principle desirable to continuously monitor the S/N of the image, and terminate the exposure when the peak is reached. Most commercial digital imaging systems make no provision for this. Fortunately, state of the art cooled CCD cameras have so little dark noise per pixel (typically <0.01 electron s$^{-1}$ in inverted clock mode) that S/N would not begin to fall until almost complete exhaustion of the fluor. In practice, autofluorescences and stray light dominate system performance long before the noise threshold of the CCD is reached.

The principal design goals for a single-fluor imaging system are:

1. To achieve an adequate rate of excitation of the fluor (F).
2. To collect the fluorescence of F and image it onto the detector with high efficiency and with the necessary spatial resolution.
3. To prevent reflected and/or scattered excitation light from reaching the detector.

Design of the emission channel for a single fluor is straightforward.

The dichroic beamsplitter transition wavelength is specified at for example, 20 mn to the red of the excitation passband. This ensures a high level of rejection of exciting light reflected and/or scattered from the specimen and/or microscope optics. The emission filter cut-on is usually considerably steeper than the dichroic edge, and so can be placed practically coincident with it. The most efficient emission filter is a long-pass element. The preferred filter of this type is Schott glass, which transmits upwards of 90% of all fluorescence to the red of its cut-on, while rejecting other light (especially any excitation light that gets through the dichroic beamsplitter) to very high order—typically >10$^5$. However, it is usually inadvisable to leave the emission channel 'wide open' into the near infrared, especially with silicon detectors which have high sensitivity there.

The multiparametric imaging of the present invention not only increases the throughput of information about the system under observation and makes more efficient use of the biological material, but also can reveal spatial and temporal correlations that might otherwise be difficult to establish reliably. When a large number of different objects must be visualized, two or more labels can be used combinatorially, which permits discrimination between many more object types than there are spectrally distinguishable labels. Some examples of multi-fluor imaging are:

a. The co-distribution of proteins in structures such as microtubule networks may readily be visualized using immunolabels linked to different fluors.
b. Multiple genes may be simultaneously mapped by fluorescence in situ hybridization (FISH) to a single metaphase chromosome spread. Such signals cannot usually be discriminated reliably on the basis of intensity alone, and are usually morphologically identical (diffraction-limited points). However, they are readily discriminated by discrete or combinatorial multi-fluor labeling.
c. Identification of small chromosomal translocations is most readily done by painting with chromosome specific DNA probe libraries linked to separable fluors, used either singly or combinatorially.
d. Analysis of mixed populations of morphologically identical bacteria can also be achieved using species-specific DNA or ribosomal RNA probes coupled to separable fluors.

The primary design goal of a multi-fluor imager (in addition to those for of a single fluor imager) is to spectrally resolve the fluorescence at any pixel location into components corresponding to each fluor. Methods for spectrally resolving complex signals in fluorescent microscope images are outlined below.

There are several ways to resolve spectrally complex signals, i.e., to determine which fluors contribute to the fluorescence at a given pixel location. The most general method in principle is to spectrally disperse the 2D image along a third axis, orthogonal to the x,y axes. This amounts to imaging through an optical system with a very large amount of chromatic aberration, such that at each position on the z axis there is an image x,y that contains only a small spectral bandwidth $\lambda+\Delta\lambda$. An area detector with very small depth of field (such as a spatially filtered confocal imager) could then be moved incrementally along the z axis to obtain a family of images, each containing its own small spectral interval. A trace through the images at given x,y would constitute an emission spectrum for that pixel. Unfortunately, implementing such a scheme is technically very difficult.

If the spectrum of only a small number of objects within the image is required (such as individual stars in a telescope image), a solution is to extract the light corresponding to each object with a probe (e.g., a fiber optic) and disperse it with an imaging spectrograph onto a 1-dimensional array detector. To be useful in microscopy, such a device would have to be arbitrarily positionable in the field, and have an adjustable acceptance area.

The most reasonable method for full spectral analysis in microscopy is to image through a variable narrow band filter. An image is recorded at each wavelength; intensity values at a given pixel location through the series represent a weighted emission spectrum that can be fit to a linear combination of the known spectra of the component fluors. The coefficients are products of the relative molar amounts of the fluors with their extinction coefficients at the exciting wavelength and their fluorescence quantum yields. If the last two are known, the first is obtainable from the fit. In general, it is necessary to take several such image sets, at several excitation wavelengths, to get a unique fit. With enough iterations, this process generates a 3D surface of intensity values as a function of both excitation and emission wavelength. This comprises a complete spectral signature of the pixel, giving a very highly constrained solution for the relative amounts of its component fluors. The mole ratios could be mapped back onto the x,y coordinates of the image, with appropriate pseudocolor coding, to give a 'composition map'. This general (and quantitative) method has a number of technical difficulties, although none of them is insurmountable. The first is that a large number of images are required to evaluate a single microscope field. Imaging time is long, and extensive differential photobleaching of the fluors would make it impossible to achieve a self consistent "fit" to the spectral data. Instrument stability is also an issue, particularly with arc sources, the output spectra of which change throughout their life. Finally, the amount of computation required to generate a composition map would realistically limit the analysis to small image regions only.

For most applications, there is no need of a full-blown spectral analysis capability because the fluors to be analyzed are known ahead of time. Thus, it is only necessary to be able to identify which fluor is which, and, for multiplex imaging, to ascertain the relative amount of each present. A preferred approach to this category of problems involves the use filter sets that achieve a high degree of selective excitation and visualization of each component fluor. The ideal system of this type would perfectly isolate each fluorophore, i.e., "one image-one fluor" and all off-diagonal elements in the matrix of intensity coefficients would be zero. However, the facts that the spectra of typical fluorophores are 10–30% of the total available bandwidth, and emission filters must have significant bandwidths to pass usable amounts of light place severe limitations on the attainable degree of spectral isolation. Nevertheless, it is not difficult to achieve useful levels of contrast between suitably chosen fluors, such that residual crosstalk can be removed numerically.

The excitation-emission contrast (EEC) approach is in principle applicable to analysis of images involving multiple fluors with fine-grained distributions of mole fraction (e.g., fluorescence ratio imaging), subject to image S/N and the limitations of differential bleaching rates and source instability. However, it is particularly simple for the limiting case of combinatorial labeling, in which fluors are multiplexed in a strictly Boolean fashion (present=1, or absent=0). In this case, it is necessary only to be able to reliably discriminate between a 1 and a 0, for which a 10:1 intensity ratio between any fluor and its neighbors would be sufficient. However, for many useful fluors this is not achievable on the basis of excitation contrast or emission contrast alone. Simultaneous selection on the basis of both excitation and emission are required.

In some circumstances it is required to excite and image several fluors simultaneously, e.g., for direct viewing and/or color video recording. Excitation and emission optics that have no wavelength selectivity cannot be used, because the excitation light scattered into the detector would overwhelm the fluorescence by several orders of magnitude. One solution is to use multiple-bandpass filters designed for the specific set of fluors to be used. The excitation filter defines narrow passbands that overlap the fluor excitation spectra. The emission filter defines similar passbands that interdigitate between the excitation bands and overlap the fluor emission spectra (the reddest fluor could use a long-pass filter). The dichroic beamsplitter alternates between reflect (overlapping the excitation passbands) and transmit (overlapping the emission passbands).

Use of a multi-pass filter set also has an advantage even when multicolor visualization is not required, viz. the absence of geometric displacement (pixel shifts) between signals passing through the several emission passbands. However, when used with a greyscale imaging system, it is necessary to make either the excitation filter or the emission filter switchable, in order to determine which greyscale signal corresponds to which fluor. The preferred choice is to switch the excitation filter, because this causes no image displacement.

A second theoretical solution would be to excite at a wavelength where all the fluors absorb. This is often possible because many fluors are excitable to states higher than S1 using photons in the middle UV, but because of internal relaxation processes give 'normal' fluorescence. For example, many laser dyes can be excited at the nitrogen laser wavelength, 337 nm, far to the blue of their visible absorbances. It would be straightforward to block such exciting light from the emission path, using a long-pass filter (e.g., 380 nm), while allowing all fluorescences to simultaneously reach the detector. Drawbacks to the use of UV excitation include increased rates of photochemical decomposition of the fluor, and the expense of suitable UV optics. Thus, the method has not found widespread use.

The multi-bandpass method has the limitation that construction of multiple bandpass elements giving adequate contrast between more than 3 fluors is extremely difficult. A generally more powerful approach is to construct optimized filter sets for each fluor, and switch them as needed. In the case of a single fluor, the primary goal on the excitation side is high excitation flux, to give a bright image. When imaging multiple fluors, however, this becomes secondary to the goal of achieving high contrast between fluors. In the weak overlap limit, fluors may be imaged by sequentially switching filters that are designed using the same criteria as single-fluor sets (except that long-pass emission filters are proscribed for all but the longest-wavelength fluor). Crosstalk of a few percent is usually allowable, and can be compensated numerically if necessary. More generally, though, generation of adequate contrast between fluors requires both strongly selective excitation and emission. The optimum wavelengths can be found by ratioing the spectra of adjacent fluors. These wavelengths may be far from the excitation maxima, implying a significant tradeoff between signal brightness and contrast. Standard filter sets cannot be used. The need for precisely placed excitation makes it less likely that a strong excitation line will be available, and also reduces the flux available from a continuum source. It may be necessary to pulse the broadband source (arc or filament lamp) to transiently very high output levels, or to supplement it with laser sources.

The principal technical problem with serial imaging is image displacement when filters are changed i.e., the coordinate systems of the individual members of an image series are not in precise registration. This problem arises from nonidealities in the emission channel optics. Two displacement components can be identified:

i. a reproducible offset that is unique to each filter set. This component is a fixed vector, and arises mainly from imperfect parallelism (i.e., wedging) between the top and bottom faces of the emission bandpass filter. There is also a small component due to wedging in the dichroic beamsplitter, but since this element is very thin the effect is minor. Since the wedging vector is a constant for each filter set, it can be automatically removed in the computer. The size of the offset can also be reduced to very small values (<0.1µ) by selecting emission filters for a high degree of parallelism e.g., by measurement in a laser autocollimator.

ii. a random component due to vibration and hysteresis in the filter switching mechanism. The magnitude of the noise depends on the filter switching mechanism. The worst are manual push-pull sliders, particularly when the operator actuates them using uncompensated forces. The best are motorized filter cassettes, in which all mechanical torques act against the microscope body.

Note that both the constant and random components of the image offset noise are minimized by using an objective lens of the highest possible magnification, and the minimum amount of magnification in the camera projection optics. Image displacements encountered in optical microscopy are linear vectors only; there is no evidence for rotation or significant changes in scale (magnification).

Design considerations for high contrast imaging of multiple overlapping fluors are similar to those already outlined for the excitation channel. By calculating the ratio of each fluor's emission spectrum to that of its neighbors, it is possible to identify spectral regions of high contrast that can be defined with narrowband filters. High contrast is often achievable only at the cost of throwing away significant amounts of the fluorescence (90% or more). Inefficiency in the fluorescence channel is much more damaging to image S/N than excitation inefficiency. Thus, where possible, selective excitation is the preferred method of achieving contrast between multiple fluors. In difficult cases, however, both excitation and emission contrast are required.

2. Optical Filter

As indicated, in a preferred embodiment of the invention, the detection of fluor is accomplished using optical filters, in a modification of the method of Ried, T. et al. (*Proc. Natl. Acad. Sci. (U.S.A.)* 89:1388–1392 (1992), herein incorporated by reference).

Imaging DAPI

4',6-diamidino-2-phenylindole (DAPI) is a commonly used DNA counterstain that intercalates preferentially into AT-rich regions of chromosomes and so gives rise to a weak G-type banding pattern. It is a very bright fluor ($\epsilon=3.3\times 10^4 M^{-1} cm^{-1}$ at 347 nm, with approx. 20-fold enhancement of fluorescence quantum yield when intercalated into the minor groove of double-stranded DNA), and is relatively resistant to photobleaching. The following points are relevant to imaging DAPI with high contrast against its neighbors:

a. DAPI has very broad excitation and emission spectra, and a very large Stoke's shift. Thus, although the DAPI excitation maximum (347 nm) is to the blue of Cascade Blue (CB), the fluorescence of DAPI peaks to the red of Cascade Blue, and actually overlaps quite strongly with FITC.

b. The usual excitation wavelength for DAPI (Hg 366 nm line) cannot be used in this application, because it is almost isosbestic for DAPI and CB and thus gives no excitation contrast.

c. The peak of the DAPI/CB excitation contrast spectrum is at 320 nm, which is too far into the UV to pass through the microscope optics. An acceptable compromise is to excite with the Hg 334.1 nm line, which the microscope transmits with about 30% efficiency. The Ealing 35-2989 interference filter has an appropriate bandpass. The excitation contrast ratio for DAPI/CB at 334.1 nm has an absolute value of 4.0.

d. To further increase the DAPI/CB selectivity, emission contrast must be used in addition to excitation contrast. Note that DAPI emits the bulk of its fluorescence to the red of CB. The wavelength of maximum emission contrast for DAPI vs. both CB and FITC is 490 nm. A suitable imaging-grade filter is the Omega 485DF22. There are no mercury lines within its bandpass, so good DAPI images with low flare are expected. The calculated emission contrast between DAPI and both Cascade Blue and FITC is 6.8. Hence, the overall contrast achievable for DAPI vs. Cascade Blue is approximately 27-fold. The overall contrast of DAPI vs. FITC is very much higher than this, because at the DAPI excitation wavelength the excitation of FITC is close to zero.

e. The Omega 450DRLP02 dichroic beamsplitter is very well matched to the proposed excitation and emission filters.

Imaging Cascade Blue

Cascade Blue (CB) has a broad, two-peak excitation spectrum that overlaps DAPI extensively, though not its neighbor on the red side (FITC). The Stokes shift for CB is very small, i.e., there is very extensive overlap between its excitation and emission spectra. These factors combine to make imaging CB in the presence of DAPI problematical. To summarize:

a. The peak of the CB/DAPI excitation contrast spectrum is at 396–404 nm. However, because of the very small Stokes' shift of CB this is very close to the emission contrast peak (408 nm). Since it is more important for image S/N to collect the emission with high efficiency than to excite with high efficiency, the 400–410 nm region is reserved for the CB fluorescence. The best compromise for CB excitation is the Omega 38OHT15, which overlaps with the Hg 366 nm line enough to provide good excitation strength.

b. To achieve any emission contrast at all vs. DAPI, the emission filter must be narrow and very carefully placed. A suitable filter is the Omega 405DF10, but the theoretical maximum contrast is only 2.5. Thus, imaging CB while excluding DAPI is expected to be marginal.

c. Cascade Blue exhibits high excitation contrast vs. FITC (contrast ratio with the Omega 38OHT15 filter=6).

d. The emission contrast ratio for CB/FITC goes to very large values below 490 nm, and is essentially infinite at the position of the 405DF10 filter.

The above considerations indicate that it will be possible to use either DAPI or Cascade Blue, but not both together unless the DAPI counterstain is weak. Cascade Blue is well separable from FITC and the other five combinatorial fluors considered herein.

Imaging FITC

The following points are relevant to high-contrast imaging of FITC:

a. The excitation spectrum of FITC has insignificant overlap with that of Cascade Blue (contrast parameter Rb for FITC/CB becomes extremely large beyond 420 nm). This makes it possible to excite FITC on the high frequency shoulder of its absorbance, so avoiding appreciable excitation of Cy3.

b. There is no mercury line that overlaps well with the FITC excitation spectrum. Thus, it is necessary to use the continuum to excite this fluor, as with single-fluor imaging. The gap between FITC and CB makes it possible to use a very wide excitation filter; the Omega 455DF70 is well suited to this function.

c. The Omega 455DF70 bandpass also corresponds fortuitously to the maximum in the excitation contrast ratio for FITC/Cy3 (460 nm; absolute extinction ratio $R_a$=8.8).

d. The emission spectrum of FITC overlaps that of Cy3 (on the red side) and both DAPI and CB (on the blue side) to an appreciable extent. However, because the conditions defined for FITC excitation do not excite DAPI or Cascade Blue at all, they are not relevant. The FITC/Cy3 emission contrast ratio goes to very high values below 540 nm. Thus, the Omega 530DF30 filter gives very high emission contrast, which compounds the high excitation contrast ratio for FITC vs. Cy3 (8.8) given by the 455DF70. It therefore appears possible to image FITC very cleanly.

Imaging Cy3

The following points are relevant to high-contrast imaging of Cy3:

a. The absorbance peak of Cy3 is at 551 nm, at which wavelength the excitation of FITC is essentially zero (contrast parameter Rb jumps to extremely high values to the red of 525 nm).

b. The Cy3 extinction peak overlaps strongly with the Hg 546.1 nm line.

c. The excitation contrast ratio for Cy3/Cy3.5 is everywhere small, and varies weakly with wavelength. At 551 nm, the absolute value of the excitation contrast for Cy3 vs. Cy3.5 is less than 2, and it only rises significantly far to the blue where the Cy3 absorbance is very low and FITC absorbance is high. In fact, the apparent rise in $R_a$ around 460–470 nm may be an artifact of the low absolute precision of the spectra in that region. From the above discussion, it is clear that the excitation contrast available for Cy3 vs. Cy3.5 is too low to be useful.

d. The emission contrast ratio for Cy3/Cy3.5 rises abruptly below 570 nm. At the 567 nm peak of the Cy3 fluorescence, the absolute value of $S_a$ is approximately 6. This, combined with the factor 2 in the excitation contrast parameter, should just about meet the goal of a 10-fold discrimination between Cy3 and Cy3.5. The Ealing 35-3722 narrowband interference filter is suitable, although it does overlap the Hg 577/579 line significantly. Any stray light from this line getting through the 546DF10 filter is, however, expected to be well blocked by the chosen dichroic, Omega 560DRLP02.

e. The inability to differentially excite Cy3 vs. Cy3.5 means wasteful bleaching of Cy3.5 during imaging of Cy3.

Imaging Cy3.5

The following points summarize high contrast imaging with this dye:

a. The excitation contrast ratio between Cy3.5 and Cy3 rises to very high values beyond approximately 565 nm. This region includes the peak of the Cy3.5 excitation spectrum.

b. The mercury arc line at 577/579 nm is almost exactly coincident with the peak of the Cy3.5 absorbance. At this wavelength the excitation contrast ratio is approximately 25, i.e., very strong selective excitation of Cy3.5 relative to Cy3 is possible. An ideal filter for this purpose is the Ealing 35-3763. Note that the high contrast is mainly a consequence of the Hg line position, not the filter bandwidth.

c. At the Hg 577/579 excitation wavelength, the excitation contrast ratio for Cy3.5 relative to Cy5 is also quite large (absolute value approximately 8.0).

d. The emission contrast parameter for Cy3.5 vs. Cy3 is small at all wavelengths where the Cy3.5 emission is usefully strong, i.e., isolation of Cy3.5 from Cy3 must rely mainly on excitation contrast.

e. The emission contrast for Cy3.5 vs. Cy5 is also large over a considerable spectral interval (and rises to very high values below 640 nm). This permits a fairly broadband filter to be used to image Cy3.5; a suitable element is the Omega 615DF45. Almost no bleadthrough of either Cy3 or Cy5 into the Cy3.5 channel is expected with the above combination of excitation and emission conditions.

f. The Omega 590DRLP02 is a suitable dichroic for this channel.

Imaging Cy5

The following points are relevant to imaging with this dye:

a. Beyond 600 nm, the excitation contrast ratio for Cy5 vs. Cy3.5 gets very large, i.e., very high excitation contrast relative to Cy3.5 is possible.

b. The placement of the Cy5 excitation is determined by the extinction ratio relative to Cy5.5 rather than Cy3.5. The Cy5/Cy5.5 excitation contrast parameter peaks at 650 nm with a numerical value of 2.25. Thus, analogous with the Cy3/Cy3.5 pair, excitation contrast for Cy5/Cy5.5 is poor.

c. There is no Hg line available for exciting Cy5. Thus, with an arc source, the continuum must be used, analogously with FITC excitation. The "official" filter for exciting Cy5 in this way is the Omega 640DF20, which will give an excitation contrast with Cy5 of about 1.8.

d. A much brighter source for exciting Cy5 is the He-Ne laser (632.8 nm). It does not, however, improve excitation contrast vs. Cy5.5.

e. The emission contrast for Cy5 vs. Cy3.5 peaks at 673 nm, just to the red of the fluorescence intensity peak. The closest available filter is the Omega 660DF32 where the emission contrast ratio is approximately 3.1. This compounds the very high excitation contrast for Cy5 vs. Cy3.

f. The emission contrast for Cy5 vs. Cy5.5 goes to very large values at wavelengths shorter than 675 nm. The Omega 660DF32 filter is ideally set up to take full advantage of this. Unfortunately, it is uncomfortably close to the 640DF20 exciter, so some flare from reflected/scattered excitation light is to be expected. Use of the He-Ne laser would remove this problem.

g. The best available dichroic beamsplitter for Cy5 imaging is the Omega 645DRLP02, particularly if a He-Ne is used as the excitation source.

Imaging Cy5.5

CY5.5 is the penultimate dye of the set, and is very well separated from Cy7. Thus, only its contrast relative to Cy5 need be considered in detail:

a. The contrast parameter Rb for the Cy5.5/Cy5 pair rises to large values to the red of 670 nm. Thus, it is possible to achieve very high excitation contrast for this pair of fluors (analogously to Cy3.5/Cy3).

b. As with Cy5, the Hg arc is a poor source for exciting Cy5.5. The best available source is a 680 nm diode-pumped frequency doubled YAG microlaser (Amoco), which coincides with the peak of the Cy5.5 absorbance. At 680 nm, the excitation contrast ratio for Cy5.5/Cy5 is 5.1. A suitable excitation filter is the Ealing 35-4068.

c. The emission contrast ratio between Cy5.5 and Cy5 peaks at 705 nm, approximately 3 nm to the red of the Cy5.5 intensity curve. The numerical value for $S_b$ at this point is 4. If the Omega 700EFLP longpass emission filter is used, a contrast ratio of approximately 3 (averaged out to 800 nm) is expected. This, combined with the high excitation contrast, makes imaging Cy5.5 very clean.

d. At the expense of slightly lower emission contrast (this would not be significant) and some loss of intensity, a bandpass filter such as the Ealing 35-6345 could be substituted for the Omega 700EFLP. The potential advantage would be reduction of the infra-red background, i.e., overall improved image contrast.

Imaging Cy7

Cy7 is the reddest dye of the set. The excitation and emission spectra are well separated from Cy5.5, and are well matched to the Omega 740DF25/770DRLP02/780EFLP triplet. The Oriel 58895 is an appropriate IR blocker for Cy7.

Filters selected for imaging the DAPI, FITC, Cy3, Cy3.5, Cy5, Cy5.5, Cy7 fluor set are summarized in the Table 2 below. None of these filter sets correspond to the filter sets supplied by manufacturers of conventional fluorescence microscopes as narrow band excitation and fluorescence detection is mandatory to achieve sufficient contrast.

TABLE 2

| | Epicube Filter Configuration (for 75 W Xe Arc Source) | | | |
| --- | --- | --- | --- | --- |
| Fluor | Excitation Bandpass Filter | Dichroic Beamsplitter | Emission Bandpass Filter | IR Blocking |
| DAPI | Zeiss 365 nm | Zeiss 395 nm | Zeiss >397 nm | None |
| FITC | Omega 455DF70 | Omega 505DRLP02 | Omega 530DF30 | BG38 |
| Cy3 | Omega 546DF10 | Omega 560DRLP02 | Ealing 35-3722 | BG38 |
| Cy3.5 | Ealing 35-3763 | Omega 590DRLP02 | Zeiss 630/30 | BG38 |
| Cy5 | Omega 640DF20 | Omega 645DRLP02 | Omega 670DF32 | Oriel 58893 |
| Cy5.5 | Ealing 35-4068 | Omega DRLP02 | Omega 700EFLP | Oriel 58893 |
| Cy7 | Omega 740DF2S | Omega 770DRLP02 | Omega 780EFLP | Oriel 58895 |

Characteristics of the microscope system are described in detail by Ballard S. G. et al. (*J. Histochem. Cytochem.* 41:1755–1759 (1993), herein incorporated by reference). A high pressure 75 W DC xenon arc (XBO) was used as an excitation source because of its approximately constant spectral power distribution. A Zeiss Axioskop microscope workstation equipped with a cooled CCD camera (Photometrics CH250) was employed. The objective lens was a 63× 1.25NA Plan Neofluar which should be "plan" and apochromatic with a high numerical aperture. The filter sets selected were able to discriminate between the six fluors with a maximum contrast (Table 2). To minimize the crosstalk between fluorophores, the filter sets were selected on the basis of maximum spectral discrimination rather than maximum photon throughput. Image exposure times were varied to adjust for photon flux differences and flux excitation cross-sections. Narrow band excitation and fluorescence detection is mandatory to achieve sufficient contrast. Appropriate excitation and emission filter sets were used to optically discriminated these fluors (Table 2).

The combinatorial labeling strategy relies on accurate measurements of intensity values for each fluorophore. Critical features are accurate alignment of the different images, correction of chromatic aberrations, and specific quantitation of each fluorophore. Because simple manual image manipulation could not realize these demands new software was developed in our lab. This program comprises the following steps in sequential order: (1) correction of the geometric image shift; (2) calculation of a DAPI segmentation mask; (3) for each combinatorial fluor, calculation and subtraction of background intensity values, calculation of a threshold value and creation of a segmentation mask; (4) use of this segmentation mask of each fluor to establish a "Boolean" signature of each probe; (5) for each chromosome, display of the chromosome material next to the DAPI image; (6) create a composite gray value image, where each labeled object is encoded with a unique gray value; (7) final presentation of the results using a look-up-table (LUT) that assigns each gray value a particular color.

The above-described program was developed on the basis of an image analysis package (BDS-Image) implemented on a Macintosh Quadra 900. Image shifts caused by optical and mechanical imperfections were corrected by the alignment of the gravity center (center of mass) of a single chromosome in each image according to a procedure described by Waggoner, A. et al. (*Methods Cell Biol* 30:449–478 (1989)) and modified (du Manoir, S. et al., *Cytometry* 9:4–9 (1995); du Manoir, S. et al., *Cytometry* 9:21–49 (1995), all herein incorporated by reference). The DAPI image was used to define the morphological boundary of each chromosome. Accurate chromosome segmentation was achieved by pre-filtering the images through a top-hat filter (Smith, T. G., et al., *J. Neurosci Methods* 26:75–81 (1988); modified in du Manoir, S. et al., *Cytometry* 9:4–9 (1995); du Manoir, S. et al., *Cytometry* 9:21–49 (1995)). The mode of the gray level histogram of the top-hat filtered DAPI image was used as the threshold. For each fluor background was eliminated by subtracting the mean interchromosomal fluorescence intensity from the image. The mean of the chromosomal fluorescence intensities was used to calculate the threshold for the individual segmentation mask of each fluor. Individual DNA targets were assigned distinct gray values depending on the "Boolean" signature of each probe, i.e. combination of fluors used to label this DNA probe. In a final step a look-up table was used to assign each DNA target a pseudocolor depending on this gray value, for display.

Switching the filter sets in excitation and emission path as well as the dichroic mirror was done manually, but a computer-controlled electro-mechanical solution will allow automation of the procedure.

3. Optical Combs

In an alternative embodiment, selective excitation of multiple fluors and analysis of fluorescence spectral signatures can be carried out using dispersion optics rather than wavelength-selective transmission filters. Such optics may be used to create filters of any passband characteristic, including short-pass, long-pass, single bandpass and multiple bandpass functions. In this method, a dispersion element (prism or grating) is used in conjunction with a wavelength-selective spatial filter to create the desired spectral response. The combination is referred to herein as a "comb filter." Using a comb filter, the spectral distribution of the exciting light may be tailored for optimum simultaneous excitation of multiple fluors. The inverse comb filter may also be used to selectively block from the CCD camera only the wavelengths used for excitation: the remaining wavelength intervals (corresponding to the gaps between teeth of the comb) are available for spectral analysis of the fluorescence emitted by the fluors. This analysis constitutes the spectral signature.

4. Interferometers

In lieu of using the optical filters described above, an interferometer may be used in conjunction with an epi-fluorescent microscope. A light source for excitation of fluorescence that is either coherent (e.g. an Argon laser) or incoherent (e.g. a Mercury arc lamp) may be used. A Mercury-Xenon mixed gas arc lamp is preferred due to its intense Mercury lines and broad Xenon visible and near-infrared continuum.

Although any of a variety of interferometer designs (such as Michelson interferometer) may be employed, the use of a Sagnac interferometer is preferred. The Sagnac interferometer has a larger acceptance angle, greater entendue, and is less sensitive to alignment, vibration, and temperature variations than a similar Michelson interferometer.

The Sagnac interferometer is a common path interferometer. An interferometer consists of two or more interfering beams of light. In a common path interferometer there are two beams each traveling the same path but in opposite directions. The optical paths are produced by reflecting light through beamsplitters, for example.

Multiple beam interferometers operate by dividing the optical energy from a light source into two substantially equal beams of light. The two beams of light are combined after one is permitted to pass through a sample and the interference pattern (the changes in intensity of the combined light caused by the interference of two beams) is detected.

In the Sagnac interferometer, the light source is also divided into two substantially equal parts. Changing the angle of incidence of light on the beamsplitter, (by rotation of the interferometer, or rotation of an optic, such as a galvanometer driven mirror within the interferometer) causes the optical path length to be changed along one optical axis of the interferometer. This produces a fringe pattern along one axis of the detector, for example a CCD detector. The other axis of the detector can sample gray scale. As the optical path length is scanned, by rotating the interferometer or a mirror, the fringe pattern produces an interferogram at each pixel. The Fourier Transform of this interferogram yields the spectrum of light falling on that pixel of the CCD. Thus, an advantage of the Sagnac interferometer is that it produces an optical path difference across an entire field of view, rather than at a single point.

A simple example of a Sagnac interferometer is shown in FIG. 1. Disturbances, such as a small shift of one of the optical elements, effect both beams in the same way, and hence have no effect on the measurement. This mechanical stability also makes the interferometer relatively insensitive to temperature changes as well. Thus, another advantage of the common path interferometer is its intrinsic stability. Sagnac interferometers and their use are well known (see, for example, U.S. Pat. Nos. 3,924,952; 4,410,275; 4,529,312; 4,637,722; 4,671,658; 4,687,330; 4,836,676 and 5,108,183).

In one implementation of a Sagnac interferometer (J. Bruce Rafert et al., "Monolithic Fourier-Transform imaging spectrometer", *Applied Optics*, November 1995), the acceptance angle of the interferometer is determined to be:

$$q = 2n \tan^{-1}(w/8a)$$

where w/a=tan 30°, w is the aperture width of the interferometer, a is the length of each leg, and n is the index of refraction of the interferometer glass. Referring to FIG. 1, this yields a full acceptance angle of approximately 8 degrees. In other designs the acceptance angle may be different but in any case the input beam to the interferometer need not be collimated.

The interference pattern or interferogram is most preferably detected with a CCD camera (such as a Princeton Instruments frame transfer CCD camera) capable of 512× 512 pixels or larger. Since the interferogram in a Sagnac interferometer has an angular dependence, each pixel of the CCD detector measures a small interval of the interferogram. The fringe spacing of the interferogram is set such that a pixel on the CCD detector can adequately sample the interferogram. The Optical Path Difference (OPD) that a pixel can span, in order to properly sample the interferogram is given by the relation:

$$OPD_{pixel} = \lambda_{min}/4$$

where $\lambda_{min}$ is the shortest wavelength in the spectrum to be measured by the interferometer. This $OPD_{pixel}$ determines the theoretical limit of the resolving power of the interferometer.

As the OPD is being changed by the rotating mirror, the interferogram is being moved across the CCD detector, such that the maximum optical path difference is then given by the relation, $$OPD_{max} = N(OPD_{pixel})$$

where N is the linear dimension of the CCD detector in pixels. Each angular displacement of the light incident on the interferometer beamsplitter may then correspond to one or several $OPD_{pixel's}$. And, in the case of a CCD detector, one frame of CCD data is required to sample this angular displacement.

Finally then, each pixel comprises an interferogram which contains within it information about the spectrum of light falling on the pixel, the intensity of light falling on that pixel, and the x and y coordinates of the pixel. The spectrum of light may be recovered from the interferogram by the use of a computational Fourier Transform algorithm.

In practice, because of the limited dynamic range of CCD's, typically about 10,000:1, the light used to excite the fluorescence must be blocked from entering the interferometer. This excitation light is often 108 to 1012 more intense than the fluorescence that is emitted from the sample. Without blocking by using optical filtering, this excitation light would saturate the CCD. However, this filter need only be fabricated so as to block the excitation, all other wavelengths may be allowed to pass.

In one embodiment, ultra violet (UV) light is used to excite the fluorescent probes. The UV light may be easily blocked with a long pass interference filter allowing the visible and near-infrared colors to pass through to the interferometer. This embodiment has the advantage that UV will excite many of the fluorescent dyes currently in use. This embodiment also has the advantage that it will allow better than 90% transmittance of the visible fluorescence to the interferometer. The disadvantage of UV is that it photobleaches the dyes faster than visible light.

Both the input and the output lens of the interferometer are preferably very high efficiency camera lenses, and do not significantly effect the efficiency of imaging. The focus of the image within the interferometer is most preferably adjusted so as to be constant for the variable powers of the zoom eyepiece, and thus a microscope having the characteristic of infinite image distance (such as Olympus AX70 microscope) are preferred.

The above-described interferometer possesses certain advantages over optical filters. One key advantage is that all the light emitted by fluorescence is theoretically available for detection, whereas the transmittance of an interference filter is limited. Another advantage is that since the filters do not have to be changed, there is no image shift due to the non-parallelism of filters.

E. Uses of the Present Invention

The capacity of the FISH (Fluorescent In Situ Hybridization) methods and reagents of the present invention to detect and analyze chromosomal abnormalities, such as translocations, inversions, duplications, etc. can be used for a large number of applications.

Among its primary applications is the cytogenetic diagnosis of genetic disease, such as the pre- or post-natal diagnosis of disease, complex tumor karyotyping, the analysis of cryptic translocations. It provides a novel method for automated chromosome identification and analysis. A large number of diseases (prenatal disease, cancers (especially BRCA1 or BRCA2 associated breast cancer), leukemias, Down's Syndrome, etc.) are characterized by rearrangements and other chromosomal abnormalities that can be discerned using the methods of the invention.

Chromosome karyotyping by conventional cytogenetic banding methods is both time consuming, expensive and not easily automated. The detection of recurring genetic changes in solid tumor tissues by karyotyping are particularly problematic because of the difficulty in routinely preparing metaphase spreads of sufficient quality and quantity and the complex nature of many of the chromosomal changes, which make marker chromosome identification based solely on banding patterns extremely difficult. Indeed, attempts to automate karyotype analysis over the past twenty years (e.g., pattern matching, eigen analysis) have failed because robust computer algorithms could not be developed to reliably decipher complex banding patterns, particularly those of extensively rearranged chromosomes.

It has been proposed that the next generation of cytogenetic techniques would be far superior by using bands that are defined molecularly by hybridization of probes or probe sets each labeled with a different color (Nederlof, P. M. et al., Cytometry 11:126–131 (1990); Nederlof, P. M. et al., Cytometry 13:839–845 (1992); Lengauer, C. et al., Hum Mol Genet 2:505–512 (1993)). This would provide a high versatility and would constitute a quantum leap well comparable to the introduction of chromosome banding and high resolution analysis of chromosomes in prometaphase. Advantages of the FISH karyotype are the instant identification of the chromosomal origin of marker chromosomes, double-minutes and homolgy staining regions ("HSRs"). Even "poor quality" chromosome spreads can be evaluated. If desired, one could design a probe set for particular applications or for particular clinical applications, e.g. hematologic diseases, pre- or postnatal diagnosis. The development of specific probe sets that stain particular regions of chromosomes (e.g. telomeric regions) for the identification of cryptic translocations would overcome limitations of the whole chromosome painting probes. Similarly, such probes could be used to generate multicolor "barcodes" on individual chromosomes thereby facilitating the automated analysis of karyotype. Probes can also be designed that would be specific for a particular arm of a chromosome, thereby permitting a molecular characterization of translocation breakpoints, hot spots of recombination, etc. Other applications would include rapid evolutionary studies, provided that the protocols for multicolor FISH on human chromosomes can be adjusted, as expected, for applications on other species.

The methods of the invention may also be used to assess the presence or absence of infectious agents (treponema pallidum, rickettsia, borrelia, hepatitis virus, HIV, influenza virus, herpes, Group B streptococcus, diarrhea-causing agents, pathogens causing acute meningitis, etc.) in tissue, or in blood or blood products. This can be accomplished by employing labeled probes specific for such agents. Moreover, by employing serotype-specific probes, the methods of the present invention permit the rapid serotyping of such agents, or the determination of whether any uch agents carry drug resistance determinants. The methods of the present invention may be used to assess chromosomal abnormalities caused by exposure to radiation (such as personnel exposed to the radioactivity of nuclear power plants).

The methods of the present invention may be used to quantitate microorganisms that are difficult to propagate (such as anaerobic microorganisms involved in periodontal disease). The methods of the present invention provide a means for the rapid diagnosis of acute bacterial meningitis. Just as one can employ serotype-specific probes to perform serological analysis, one can employ probes that are specific to particular drug resistance determinants, and thereby rapidly determine not only the presence and identity of an infectious agent, but also its susceptibility or resistance to particular antibiotics.

The methods of the present invention further permit simultaneous mapping of a large number of different DNA probes. With this technique the analysis of chromosomal number and architecture in individual intact cells becomes accessible. Interphase cytogenetics is already possible with small region specific probes, e.g. YAC-clones. The accuracy of such analysis could be increased by a three dimensional analysis using a laser scanning microscope. In addition, the use of a laser scanning microscope would ultimately allow to visualize all whole chromosome painting probes in interphase nuclei and questions relating to intranuclear chromosomal organization as a function of developmental status, cell cycle or disease state could be addressed. Different models about the chromosomal organization in interphase nuclei could finally be explored. Although conventional laser scanning microscopes currently do not allow the excitation of some of the fluorophores used, other, more appropriate fluors or devices may be employed.

Extended to non-mitotic cells, the methods of the present invention enable one to examine chromosome architecture or quantitate the chromosome contents of nuclei in single hybridization experiments. Questions relating to intranuclear chromosomal organization as a function of developmental status, cell cycle or disease state can accordingly be addressed. In addition, the ability to quantitatively assess the levels of multiple mRNAs or proteins in a single cell or to determine if they exhibit different intracellular distributions could prove extremely useful in addressing a myriad of interesting biological questions. The multiparametric imaging of the present invention does not merely increases the throughput of information, it also makes more efficient use of the biological material. Thus, it can reveal spatial and temporal correlations as well as mosaicisms that might otherwise be difficult to establish reliably. Since the intracellular distribution of mRNAs and protein is not known a priori to be spatially distinct, as in the case for the intranuclear chromosome domains, it will not be possible to use the combinatorial labeling strategies in these experiments. However, many mRNAs and protein antigens are spectrally resolvable and detectable. Thus, for the first time the intracellular distribution of oncoproteins or tumor suppressor proteins can be determined within the same cell simultaneously.

F. Automated Karyotypic Analyses

One aspect of the present invention relates to automated, preferably computer-facilitated, karyotypic analyses. As described above, in one embodiment of the invention, the chromosomes of a particular karyotype are pseudo-colored to thereby facilitate the assignment of the chromosomes, or the recognition of translocations, deletions, etc. In one sub-embodiment thereof, the digitized images of the chromosomes may be stored in computerreadable storage device (such as a magnetic or optical disk) to facilitate their comparison with other chromosomal images or their transmission and study. In this regard, probes may be employed that are translocation specific or specific to sub-chromosomal elements or regions, such that the pseudocoloration process displays banded or striped chromosomal images. The position and sizes of individual bands is preferably digitized and stored so that an image of the chromosome may be -stored on a computer. Similarly, the precise position of any translocation or other karyotypic abnormality can be discerned and stored.

The methods of the present invention thus permit karyotypic analyses to be conducted more widely and more accurately than was previously feasible. The present invention may thus be used to systematically correlate karyotypic abnormalities with disease or conditions. For example, karyotypes of asymptomatic individuals can be obtained and evaluated in light of any subsequent illness (e.g., cancer, Alzheimer's disease, etc.) or condition (e.g., hypertension, atherosclerosis, etc.) in order to permit a correlation to be made between a patient's karyotype and his or her predisposition to different diseases and conditions. Similarly, karyotypes of individuals having diagnosed diseases or conditions can be obtained and evaluated in light of the extent of any subsequent progression or remission of the disease or condition so as to permit a correlation to be made between a particular karyotype and the future course of a disease or condition.

In a further sub-embodiment, a computer or other digital signal analyzer may be employed to orient and arrange the chromosomal images as well as assigning and identifying the chromosomes of the karyotype. Thus, a computer or other data processor will, upon assigning a particular chromosome to a particular designation (for example, upon assigning that a particular chromosomal image is the image of the chromosome 7 of the karyotype being evaluated), group the assigned chromosome with its homologue (e.g., the second chromosome 7 of the patient's karyotype) and generate, via a printer, monitor, or other output means, an ordered array of chromosomal images in which each autosomal chromosome is paired with its homologue, and in which the sex chromosomes X and Y are paired together.

In one sub-embodiment, the chromosomal images of such arrays will be the pseudocolorized images discussed above. Alternatively, such psudocoloring may be internal to the process of assigning chromosomal identity, and not displayed in the output of the computer or digital signal analyzer. Rather, in this sub-embodiment, the output generated will be the light-microscope visible banding pattern of the metaphase chromosomes of the patient whose karyotype is being evaluated. In a further sub-embodiment, a scale (in Morgans or other suitable units) will be superimposed upon the chromosomal images.

Having now generally described the invention, the same will be more readily understood through reference to the following examples which are provided by way of illustration, and are not intended to be limiting of the present invention, unless specified.

EXAMPLE 1

Combinatorial Labeling of Chromosomes

In order to test the feasibility to produce 24 colors chromosome painting probes representing the 22 autosomes and the two sex chromosomes were used. The DNA probes used were generated by microdissection.

Microdissected probes (National Center for Human Genome Research, Bethesda, Md.) give a very uniform labeling of the target region. The detailed protocols for microdissection and PCR amplification are described by Telenius et al. (Telenius, H. et al., Genes, Chromosomes & Cancer 4:257–263 (1992); Telenius, H. et al., Genomics 13:718–725 (1992); Meltzer, P. S. et al., Nature Genetics 1:24–28 (1992); Guan, X. Y. et al., Hum Mol Genet 2:1117–1121 (1993); Guan, X. Y. et al., Genomics 22:101–107 (1994); Guan, X. Y. et al., Hum Genetics 95:637–640 (1995), all herein incorporated by reference). For some chromosomes different DNA-probes for the p- and the q-arms were available, namely 2, 4, 5, 10, 11, 16, 18, and Y. For all other chromosomes microdissected probes painting the entire chromosome were used.

The first member of the set of preferred fluors, DAPI, was used as a general DNA counterstain. The remaining fluors: fluorescein, Cy3, Cy3.5 (emission and excitation spectra are between Cy3 and Cy5), Cy5 (Mujumdar, R. B. et al., Cytometry 10: 11–19 (1989), and Cy7 (emitting to the red of Cy5 (Ernst, L. A., et al., Cytometry 10:3–10 (1989)), were used to combinatorially label different probes (Table 3). Distinctive features of these dyes are high extinction coefficients, quantum yields, and photostabilities. Fluorescein is a xanthene dye with an extinction coefficient around 70,000 L/mol cm and quantum yields in optimal buffers around 0.7. The respective values for cyanines are 1-200,000 and 0.3 (Waggoner, A., Methods in Enzymology 246:362–373 (1995)).

After microdisection, the probes were subjected to a PCR amplification and labeled by nick translation. Fluorescein (Wiegant, J. et al., Nuc Acids Res 19:3237–3241 (1991)), Cy3, and Cy5 were directly linked to DUTP for direct labeling. Cy3.5 and Cy7 were available as avidin or anti-digoxin conjugates for secondary detection of biotinylated or digoxinigated probes. They were synthesized using conventional N-succinamide ester coupling chemistry. For each probe one to three separate nick translation reactions were necessary, each with a single labeled fluor-labeled triphosphate or biotin or digoxigenin (Table 3).

TABLE 3

| Fluor | Chromosome | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| FITC | X | | | | | X | X | | X | | | |
| Cy3 | | X | | X | | X | | | X | | | X |
| Cy3.5 | | | X | | X | X | | | | | X | X |
| Cy5 | | | | | | | | | X | X | X | |
| Cy7 | | X | | | X | | | X | | | | X |

| Fluor | Chromosome | | | | | | | | | | | |
|---|---|---|---|---|---|---|---|---|---|---|---|---|
| | 13 | 14 | 15 | 16 | 17 | 18 | 19 | 20 | 21 | 22 | X | Y |
| FITC | X | | X | | X | | X | X | X | | | X |
| Cy3 | X | | X | | X | | | | X | | X | X |
| Cy3.5 | | X | X | | X | X | | X | | X | | |
| Cy5 | | X | | X | | X | X | X | X | | | |
| Cy7 | X | X | X | | X | X | | X | | | | |

As expected probes labeled with equal amounts of different fluors did not give equivalent signal intensities for each fluor reflecting the fact that the filter sets were selected to maximize spectral discrimination rather than photon throughput. In order to diminish signal intensity -differentials, probe concentrations for the hybridization mix had to be established carefully in a large number of control experiments. Hybridization conditions were optimized for these multiplex probes. Thus, probes were denatured and hybridized for two to three nights at 37° C. to metaphase chromosome spreads in a conventional 50% formamide hybridization cocktail. The slides were washed at 45° C. in 50% formamide/2×SSC three times followed by three washes at 60° C. in 0.1×SSC to remove excess probe. After a blocking step in 4×SSC/3% bovine serum albumin for 30 min at 37° C. the biotinylated probes were detected with avidin Cy3.5 and the dig-labeled probes with anti-dig-Cy7. Fluorescein-dUTP, Cy3-dUTP, and Cy5-dUTP did not require any immunological detection step. After final washes at 45° C. with 4×SSC/0.1% Tween 20 three times, mounting medium and a coverslip were applied and the hybridization signals from each fluor imaged using the filters sets listed in Table 3.

FIG. 1 provides a schematic illustration of the CCD camera and microscope employed in accordance with the present methods.

FIG. 2 shows the raw data from a karyotypic analysis of chromosomes from a bone marrow patient (BM2486). Adjacent to each source image is a chromosome "mask" generated by the software program. In FIG. 2, panels A and B are the DAPI image and mask; panels C and D are FITC image and mask; panels E and F are Cy3 image and mask; panels G and H are Cy3.5 image and mask; panels I and J are Cy5 image and mask; and panels K and L are Cy7 image and mask.

Figure 3A:
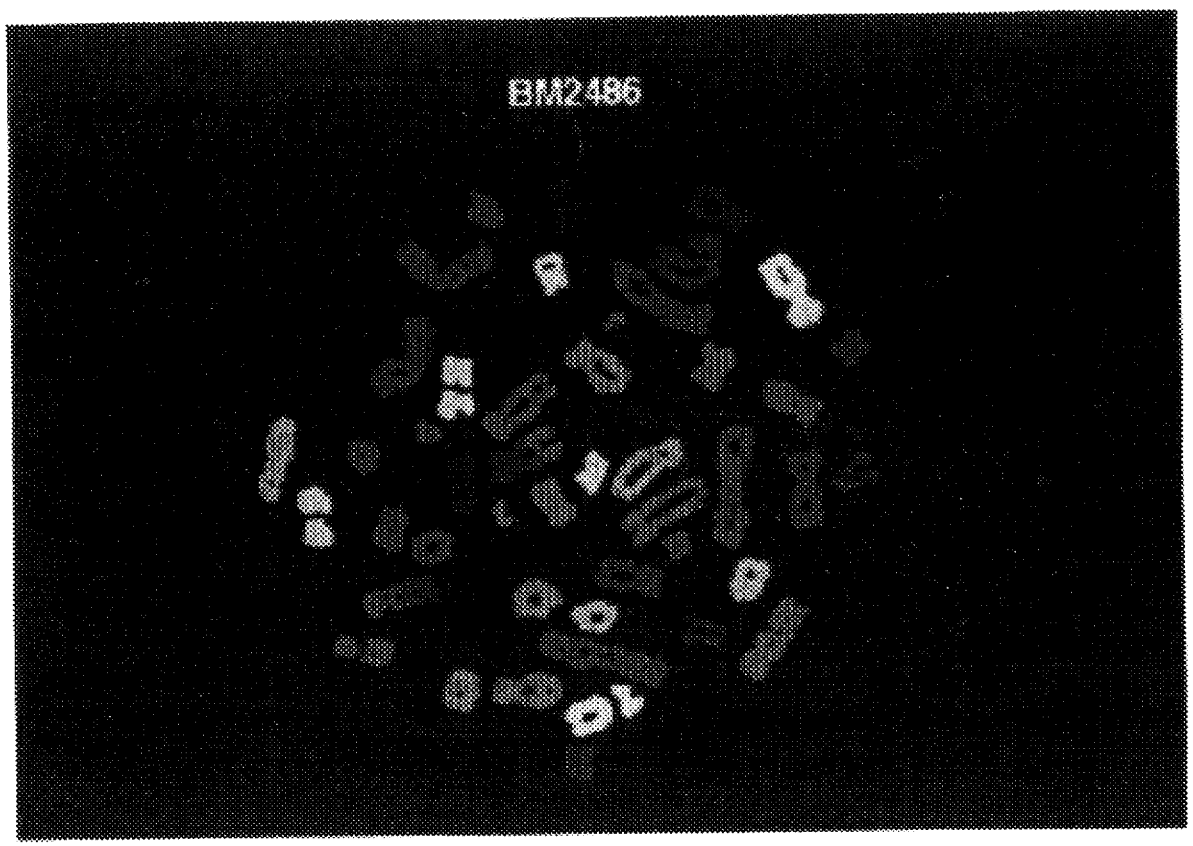
FIGS. 3A and 3B show the identification of individual chromosomes by spectral signature of patient BM2486.
Figure 3B:
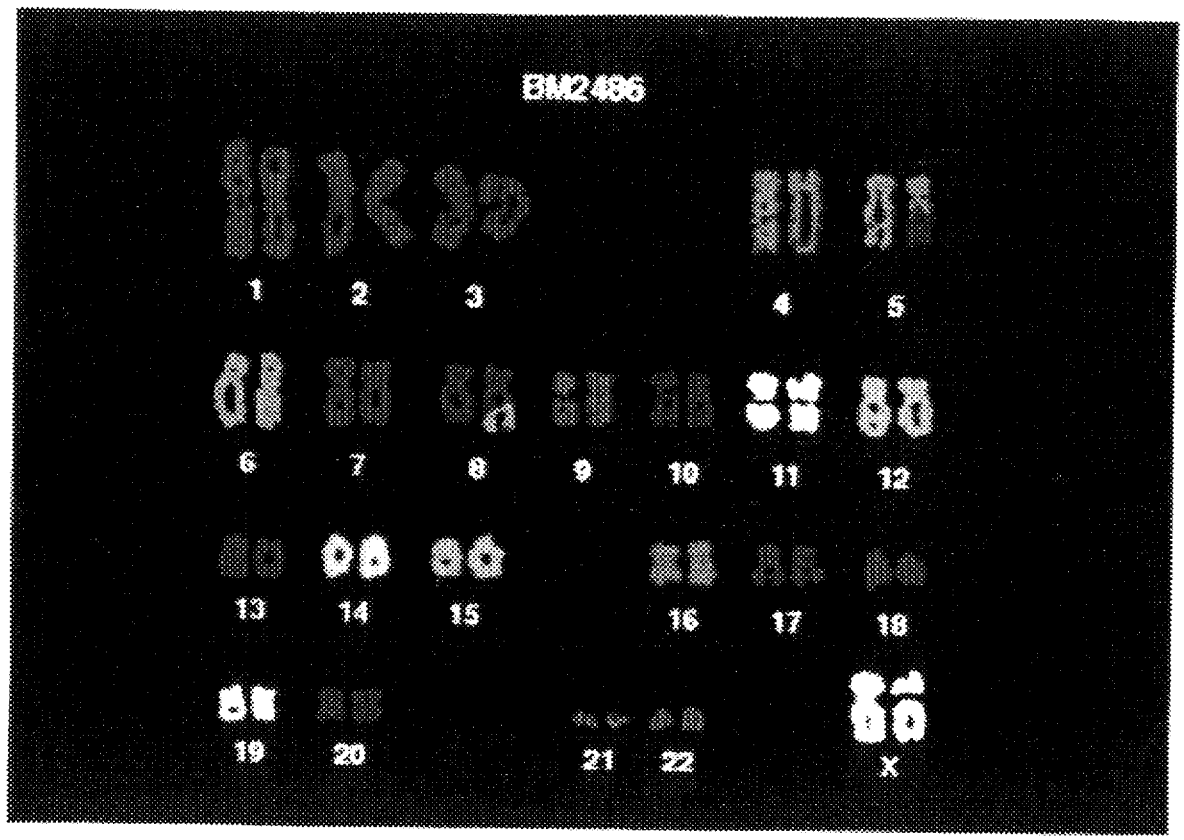

FIGS. 3A and 3B show the identification of individual chromosomes by spectral signature. FIG. 3A is the same photograph as FIG. 2, except that it is gray scale pseudocolored. FIG. 3B displays the karyotypic array of the chromosomes. The exceptional power of the methods of the present invention are illustrated by the ease with which the translocation of chromosomes 5 and 8 are identified in FIGS. 3A and 3B, relative to conventional non-chromosome specific karyotype analysis.

The above experiment demonstrates that five fluors can be spectrally discriminated to produce at least twenty four different colors. The combinatorial labeling schemes need not be as complex as previously thought, because using 5 fluors for probe labeling, only 9 painting probes need to be labeled with as many as three fluors. A sixth fluor for probe labeling would allow up to 63 possible fluor combinations. Such a high number of different targets will not be required for most applications, but would allow the selection of combinations with the best spectral signature. These above-described protocols allow highly reliable and reproducible multicolor FISH.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of simultaneously identifying and distinguishing the individual autosomal and sex chromosomes of a human karyotype which comprises the steps:

(a) contacting a preparation of said chromosomes, in single-stranded form, under conditions sufficient to permit nucleic acid hybridization to occur with a set of combinatorially labeled oligonucleotide probes, each member thereof: (i) having a predetermined fluorescent label distinguishable from the label of any other member of said set, and (ii) being capable of specifically hybridizing with one predetermined autosomal or sex chromosome of a human karyotype; said set having sufficient members to be capable of specifically hybridizing each autosomal and sex chromosome of said human karyotype; wherein said contacting thereby results in each autosomal or sex chromosome of said preparation being hybridized to at least one member of said set of probes;

(b) for each chromosome of said preparation hybridized to at least one member of said set of probes, employing an interferometer to detect and identify the predetermined label of the hybridized probe member(s) to correlate the identity of the label with the identity of the autosomal and sex chromosomes of said human karyotype, thereby identifying the chromosome hybridized to said probe member(s); and (c) repeating step (b) until each autosomal and sex chromosome of said human karyotype has been identified in said preparation.

2. The method of claim 1, wherein said interferometer is a common path interferometer.

3. The method of claim 2, wherein said common path interferometer is a Sagnac interferometer.

4. The method of claim 1, wherein, in step (b), an interferogram is produced from said interferometer, and said interferogram is Fourier transformed to recover a spectral signature of the predetermined label of said hybridized probe member.

5. The method of claim 4, wherein the spectral signature of the predetermined label of said hybridized probe member in step (b) is recovered by comparing said interferogram to a library or lookup table of previously determined interferograms.

6. The method of claim 2, wherein in step (b), an interferogram is produced from said interferometer, and said interferogram is Fourier transformed to recover a spectral signature of the predetermined label of said hybridized probe member.

7. The method of claim 6, wherein the spectral signature of the predetermined label of said hybridized probe member in step (b) is recovered by comparing said interferogram to a library or lookup table of previously determined interferograms.

8. The method of claim 3, wherein, in step (b), an interferogram is produced from said interferometer, and said interferogram is Fourier transformed to recover the spectral signature of the predetermined label of said hybridized probe member.

9. The method of claim 8, wherein the spectral signature of the predetermined label of said hybridized probe member in step (b) is recovered by comparing said interferogram to a library or lookup table of previously determined interferograms.

* * * * *